United States Patent [19]

Brookes et al.

[11] 4,148,626

[45] Apr. 10, 1979

[54] HERBICIDAL AGENTS

[75] Inventors: Robert F. Brookes, Tollerton; David H. Godson, Chilwell; Douglas Greenwood, Nottingham; Margaret Tulley, Mapperley; Stanley B. Wakerley, Burton Joyce, all of England

[73] Assignee: The Boots Company Limited, Nottingham, England

[21] Appl. No.: 849,367

[22] Filed: Nov. 7, 1977

Related U.S. Application Data

[60] Division of Ser. No. 603,572, Aug. 11, 1975, Pat. No. 4,087,269, which is a division of Ser. No. 317,453, Dec. 21, 1972, Pat. No. 3,952,001, which is a continuation-in-part of Ser. No. 261,206, Jun. 9, 1972, abandoned, which is a continuation-in-part of Ser. No. 153,448, Jun. 15, 1971, abandoned.

[30] Foreign Application Priority Data

Jul. 1, 1970 [GB] United Kingdom .............. 31922/70
Mar. 31, 1971 [GB] United Kingdom ................ 8275/71
Dec. 31, 1971 [GB] United Kingdom .............. 61022/71
Dec. 31, 1971 [GB] United Kingdom .............. 61023/71

[51] Int. Cl.$^2$ .................... A01N 9/16; C07D 249/12; C07D 401/12; C07D 403/12
[52] U.S. Cl. ................................. 71/92; 260/308 R; 544/132; 546/210
[58] Field of Search ..................... 260/308 R, 293.69; 544/132; 71/92

[56] References Cited

U.S. PATENT DOCUMENTS

| | | | |
|---|---|---|---|
| 3,308,131 | 3/1967 | McKusick | 260/308 R |
| 4,038,387 | 7/1977 | Doyle et al. | 544/132 |

*Primary Examiner*—Alton D. Rollins
*Attorney, Agent, or Firm*—Lawrence Rosen; E. Janet Berry

[57] ABSTRACT

Novel 1-carbamoyl-1,2,4-triazoles, processes for their production, and herbicidal compositions and methods are described. The compounds are particularly useful for the pre-weed emergence control of the graminaceous weeds crabgrass, barnyard grass, yellow foxtail and Johnson grass.

14 Claims, No Drawings

HERBICIDAL AGENTS

This application is a division of application Ser. No. 603,572, filed Aug. 11, 1975, now U.S. Pat. No. 4,087,269, which is a division of application Ser. No. 317,453, filed Dec. 21, 1972, now U.S. Pat. No. 3,952,001, which is a continuation-in-part of copending application Ser. No. 261206, filed June 9, 1972, now abandoned, which is in turn a continuation-in-part of application Ser. No. 153448, filed June 15, 1971, now abandoned.

The invention relates to new chemical compounds with herbicidal activity. Moe particularly, this invention relates to new 1,2,4-triazoles, herbicidal compositions containing these compounds as active ingredients, and the use of these compounds to control weeds.

In U.S. Pat. No. 3,308,131 there is described a broad group of 1,2,4-triazoles of the isomeric general formulae

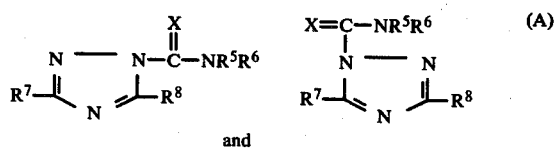

wherein X is oxygen or sulphur, $R^5$ and $R^6$ are aliphatic groups which together contain up to 14 carbon atoms and which may be joined to form a heterocyclic ring with the carbamoyl nitrogen atom, and $R^7$ and $R^8$, which together contain up to 14 carbon atoms, are free from aliphatic unsaturation and are selected from hydrogen, halogen, sulphonyl, mercapto, cyano, hydrocarbyl, halohydrocarbyl, nitrohydrocarbyl, hydrocarbyloxycarbonylhydrocarbyl, hydrocarbylsulphonyl, hydrocarbylmercapto, nitrohydrocarbylmercapto, halohydrocarbylmercapto, aminohydrocarbylmercapto and hydrocarbyloxyhydrocarbyl. The compounds in this group are stated to be effective insecticides, particularly against mites an aphids. In addition, some of the compounds are stated to have analgesic properties.

We have now found that advantageous and valuable herbicidal properties are possessed by a relatively narrow group of new 1,2,4-triazoles, some of which compounds are encompassed by the broad group of 1,2,4-triazoles defined above.

The new 1,2,4-triazoles provided by the present invention are 1-N,N-disubstituted-carbamoyl-1,2,4-triazoles with a sulphur function in the 3-position, selected from the group consisting of (a) a compound of the formula

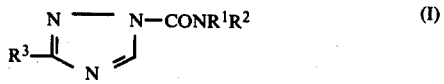

in which $R^3$ is alkylthio containing 2–5 carbon atoms, alkylsulphinyl containing 3–5 carbon atoms, alkylsulphonyl containing 1–5 carbon atoms or alkenylthio containing 3 or 4 carbon atoms, $R^1$ is alkyl containing 2–6 carbon atoms, allyl or 2-methylallyl, and $R^2$ is alkyl containing 2 or 3 carbon atoms, allyl, 2-methylallyl or prop-2-ynyl, the total number of carbon atoms in $R^1$ and $R^2$ together being 4–9 inclusive;

(b) a compound of the formula

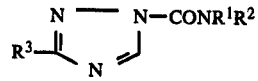

in which $R^3$ is alkylsulphonyl containing 1–5 carbon atoms, alkenyloxyalkylthio containing 4–6 carbon atoms, alkoxyalkylsulphinyl containing 2–6 carbon atoms, alkoxyalkylsulphonyl containing 2–6 carbon atoms, haloalkylsulphinyl containing 2–5 carbon atoms or haloalkylsulphonyl containing 1–5 carbon atoms, $R^1$ is alkyl containing 2–6 carbon atoms, allyl, 2-methylallyl, alkoxyalkyl containing 2–6 carbon atoms, alkenyloxyalkyl containing 4–6 carbon atoms, haloalkyl containing 2–6 carbon atoms, 2-haloallyl or 2,3-dihaloallyl, and $R^2$ is alkyl containing 2 or 3 carbon atoms, allyl, 2-methylallyl, prop-2-ynyl, alkoxyalkyl containing 2, 3 or 4 carbon atoms, haloalkyl containing 2 or 3 carbon atoms, 2,3-dihaloallyl or cyclopropyl, provided that $R^2$ is cyclopropyl or that at least one of the groups $R^1$, $R^2$ and $R^3$ contains an alkoxy substituent or one or two halo substituents; and (c) a compound of the formula

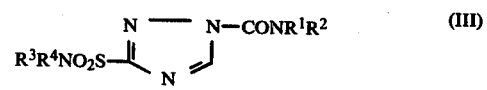

in which $R^1$ is alkyl containing 1 or 2 carbon atoms, allyl, 2-methylallyl, prop-2-ynyl, alkoxyalkyl containing 2–4 carbon atoms, haloalkyl containing 1–4 carbon atoms, 2-haloallyl, 2,3-dihaloallyl or cyclopropyl, $R^2$ is alkyl containing 2–8 carbon atoms, alkenyl containing 2–8 carbon atoms, alkenyloxyalkyl containing 4–8 carbon atoms (for example allyloxyalkyl or (2-methylallyl)oxyalkyl), haloalkyl containing 2–8 carbon atoms, 2-haloallyl, 2,3-dihaloallyl, cyclopropyl or cyclohexyl, $R^3$ is alkyl containing 1–4 carbon atoms, allyl, 2-methylallyl, prop-2-ynyl, alkoxyalkyl containing 2–4 carbon atoms, haloalkyl containing 1–4 carbon atoms, 2-haloallyl, 2,3-dihaloallyl, cyclopropyl or phenyl containing 1–3 halo substituents, $R^4$ is alkyl containing 1–8 carbon atoms, alkenyl containing 2–8 carbon atoms, alkoxyalkyl containing 2–8 carbon atoms, alkenyloxyalkyl containing 4–8 carbon atoms (for example allyloxyalkyl or (2-methylallyl)oxyalkyl), haloalkyl containing 1–8 carbon atoms, 2-haloallyl, 2,3-dihaloallyl, cyclopropyl, or cyclohexyl, or $R^3$ and $R^4$, together with the nitrogen atom to which they are attached, form a heterocyclic ring, optionally containing 1–4 lower alkyl (preferably methyl) substituents, selected from morpholino, pyrrolidino, 1-piperidyl, hexamethyleneimino and heptamethyleneimino, provided that the total number of carbon atoms in $R^1$ and $R^2$ together is 3–9 inclusive, and when $R^3$ is a radical not containing a phenyl nucleus, the total number of carbon atoms in $R^3$ and $R^4$ together is 2–9 inclusive.

COMPOUNDS OF FORMULA III

According to one feature of the present invention there are provided new compounds of the general formula III, in which $R^1$ is alkyl containing 1 or 2 carbon atoms, allyl, 2-methylallyl, prop-2-ynyl, alkoxyalkyl containing 2–4 carbon atoms, haloalkyl containing 1–4 carbon atoms, 2-haloallyl, 2,3-dihaloallyl or cyclopropyl, $R^2$ is alkyl containing 2–8 carbon atoms, alkenyl containing 2–8 carbon atoms, alkenyloxyalkyl containing 4–8 carbon atoms (for example allyloxyalkyl or (2-methylallyloxyalkyl) haloallyl containing 2–8 carbon atoms, 2-haloallyl, 2,3-dihaloallyl, cyclopropyl or cyclohexyl, $R^3$ is alkyl containing 1–4 carbon atoms, allyl, 2-methylallyl, prop-2-ynyl, alkoxyalkyl containing 2–4 carbon atoms, haloalkyl containing 1–4 carbon atoms, 2-haloallyl, 2,3-dihaloallyl, cyclopropyl or phenyl containing 1–3 halo substituents, $R^4$ is alkyl containing 1–8 carbon atoms, alkenyl containing 2–3 carbon atoms, alkoxyalkyl containing 2–8 carbon atoms, alkenyloxyalkyl containing 4–8 carbon atoms (for example allyloxyalkyl or (2-methylallyl)oxyalkyl), haloalkyl containing 1–8 carbon atoms, 2-haloallyl, 2,3-dihaloallyl, cyclopropyl, or cyclohexyl, or $R^3$ and $R^4$, together with the nitrogen atom to which they are attached, form a heterocyclic ring, optionlly containing 1–4 lower alkyl (preferably methyl) substituents, selected from morpholino, pyrrolidino, 1-piperidyl, hexamethyleneimino and heptamethyleneimino, provided that the total number of carbon atoms in $R^1$ and $R^2$ together is 3–9 inclusive, and when $R^3$ is a radical not containing a phenyl nucleus, the total number of carbon atoms in $R^3$ and $R^4$ together is 2–9 inclusive.

Preferably any alkoxy, alkenyloxy or halo substituent in an alkoxyalkyl, alkenyloxyalkyl or haloalkyl radical is attached in a position other than the alpha position, i.e., is attached to a carbon atom other than that which is attached to the nitrogen atom of the carbamoyl group -CONR$^1$R$^2$ or the nitrogen atom of the sulphamoyl group -SO$_2$NR$^3$R$^4$. Under these circumstances, when $R^4$ is alkoxyalkyl it contains 3–8 carbon atoms, when $R^2$ or $R^4$ is alkenyloxyalkyl it contains 5–8 carbon atoms and when $R^2$ or $R^4$ is haloalkyl it contains 2–8 carbon atoms.

The term "halo" includes chloro, bromo and fluoro and in the case of an aliphatic group, preferably chloro. The term "alkoxy" includes alkoxy radicals with 1, 2, 3 or 4 carbon atoms, for example methoxy, ethoxy, propoxy, isopropoxy, n-butoxy and isobutoxy. The term "lower" designates an alkyl or alkoxy radical with 1–3 carbon atoms, preferably methoxy or methyl. A peferred value of "alkenyloxyalkyl" is allyloxyalkyl, for example allyloxyethyl or 3-allyloxypropyl. Preferred values of alkenyl for $R^2$ and $R^4$ are allyl and 2-methylallyl.

The radicals $R^1$ and $R^2$ may be straight or branched chain radicals.

Typical values of $R^1$ include, for example, methyl, ethyl, allyl, 2-methylallyl, prop-2-ynyl, methoxymethyl, 2-methoxyethyl, 2-ethoxyethyl, 3-methoxypropyl, chloromethyl, 2-chloroethyl, 2-bromoethyl, 2-fluoroethyl, 3-chloropropyl, 3-bromopropyl, 4-chlorobutyl, 4-bromobutyl, 2-chloroallyl, 2-bromoallyl, 2,3-dichloroallyl, 2,3-dibromoallyl and cyclopropyl.

Typical values of $R^2$ include, for example, ethyl, propyl, isopropyl, n-butyl, isobutyl, sec.butyl, n-pentyl, isopentyl, n-hexyl, n-heptyl, n-octyl, allyl, 2-methylallyl, 2-allyloxyethyl, 3-allyloxypropyl, 2-chloroethyl, 2-bromoethyl, 2-fluoroethyl, 3-chloropropyl, 3-bromopropyl, 4-chlorobutyl, 4-bromobutyl, 3-chloropentyl, 6-chlorohexyl, 2-chloroallyl, 2-bromoallyl, 2,3-dichloroallyl, 2,3-dibromoallyl, cyclopropyl, and cyclohexyl.

Typical values of the carbamoyl group -CONR$^1$R$^2$ include dialkylcarbamoyl [for example N-methyl-N-ethylcarbamoyl, diethylcarbamoyl, N-ethyl-N-propylcarbamoyl, N-ethyl-N-isopropylcarbamoyl, N-butyl-N-ethylcarbamoyl], diallylcarbamoyl, N-allyl-N-alkylcarbamoyl wherein the alkyl radical contains 1–6 carbon atoms [for example N-allyl-N-methylcarbamoyl, N-allyl-N-ethylcarbamoyl, N-allyl-N-propylcarbamoyl, N-allyl-N-n-butylcarbamoyl, N-allyl-N-isobutylcarbamoyl, N-allyl-N-n-pentylcarbamoyl and N-allyl-N-n-hexylcarbamoyl], N-allyl-N-(2-methoxyethyl)carbamoyl, N-allyl-N-(2-ethoxyethyl)carbamoyl, N-allyl-N-(2-chloroethyl)carbamoyl, N-alkyl-N-(2-methoxyethyl)carbamoyl or N-alkyl-N-(2-ethoxyethyl)carbamoyl wherein the alkyl radical contains 2–6 carbon atoms [for example N-ethyl-N-(2-methoxyethyl)carbamoyl, N-propyl-N-(2-methoxyethyl)carbamoyl, N-ethyl-N-(2-ethoxyethyl)carbamoyl, and N-propyl-N-(2-ethoxyethyl)carbamoyl], N-methyl-N-cyclohexylcarbamoyl, N-propyl-N-prop-2-ynyl, N-alkyl-N-(2-chloroallyl)carbamoyl wherein the alkyl radical contains 2–6 carbon atoms and N-alkyl-N-(2,3-dichloroallyl)carbamoyl wherein the alkyl radical contains 2–6 carbon atoms, N-cyclopropyl-N-propylcarbamoyl, and N-cyclopropyl-N-ethylcarbamoyl.

The radicals $R^3$ and $R^4$ may be straight or branched chain radicals.

Typical values of $R^3$ include, for example, methyl, ethyl, propyl, isopropyl, n-butyl, isobutyl, sec.butyl, allyl, 2-methylallyl, prop-2-ynyl, methoxymethyl, 2-methoxyethyl, 2-ethoxyethyl, 3-methoxypropyl, chloromethyl, 2-chloroethyl, 2-bromoethyl, 2-fluoroethyl, 3-chloropropyl, 3-bromopropyl, 4-chlorobutyl, 4-bromobutyl, 2-chloroallyl, 2-bromoallyl, 2,3-dichloroallyl, 2,3-dibromoallyl, cyclopropyl, 4-chlorophenyl, 4-bromophenyl and 4-fluorophenyl.

Typical values of $R^4$ include, for example, methyl, ethyl, propyl, isopropyl, n-butyl, isobutyl, sec.butyl, n-pentyl, isopentyl, n-hexyl, m-heptyl, n-octyl, allyl, 2-methylallyl, methoxymethyl, 2-methoxyethyl, 2-ethoxyethyl, 2-propoxyethyl, 2-n-butoxyethyl, 3-methoxypropyl, 3-ethoxypropyl, 2-methoxypropyl, 2-ethoxypropyl, 2-n-butoxyethyl, 2-chloroethyl, 2-bromoethyl, 2-fluoroethyl, 3-chloropropyl, 3-bromopropyl, 4-chlorobutyl, 4-bromobutyl, 3-chloropentyl, 6-chlorohexyl, 2-chloroallyl, 2-bromoallyl, 2,3-dichloroally, 2,3-dibromoallyl, cyclopropyl, cyclohexyl, 2-allyloxyethyl and 3-allyloxypropyl.

As hereinbefore mentioned, when the group NR$^3$R$^4$ is a heterocyclic group, it may contain 1–4 lower alkyl (preferably methyl) substituents. Such alkyl-substituted heterocyclic groups include, for example, 2,6-dimethylmorpholino, 4-methyl-1-piperidyl, 2-methyl-1-piperidyl and 2,6-dimethyl-1-piperidyl.

Typical examples of the sulphamoyl group —SO$_2$NR$^3$R$^4$ include, for example, dimethylsulphamoyl, diethylsulphamoyl, dipropylsulphamoyl, di-n-butylsulphamoyl, diallylsulphamoyl, di-(2-methylallyl)-sulphamoyl, N-lower alkyl-N-cyclohexylsulphamoyl for example N-methyl-N-cyclohexylsulphamoyl, N-allyl-N-alkylsulphamoyl wherein the alkyl radical contains 1–5 carbon atoms (for example N-allyl-N-methylsulphamoyl, N-allyl-N-ethylsulphamoyl and N-allyl-N-propylsulphamoyl), N-methyl-N-alkylsulphamoyl wherein the alkyl radical contains 1–8 carbon atoms (for example N-methyl-N-ethylsulphamoyl, N-methyl-N-propylsulphamoyl, N-methyl-N-propylsulphamoyl, N-methyl-N-n-butylsulphamoyl, N-methyl-N-sec.butylsulphamoyl and N-methyl-N-isobutylsulphamoyl), N-ethyl-N-propylsulphamoyl, N-ethyl-N-isopropylsulphamoyl, N-ethyl-N-butylsulphamoyl, N-methyl-N-(4-fluorophenyl)sulphamoyl, morpholinosulphonyl, 1-pyrrolidinylsulphonyl, 1-piperidylsulphonyl, hexamethylenesulphonyl and heptamethyleneiminosulphonyl.

Preferably, $R^1$ is alkyl containing 1 or 2 carbon atoms, allyl, 2-methylallyl, prop-2-ynyl, or alkoxyalkyl containing 2–4 carbon atoms and $R^2$ is alkyl containing 2–8 carbon atoms, alkyl or 2-methylallyl. It is preferred that the carbamoyl group $CONR^1R^2$ is dialkylcarbamoyl in which the alkyl groups are the same or different and together contain 3–6 carbon atoms, diallylcarbamoyl, H-allyl-N-alkylcarbamoyl in which the alkyl group contains 1–4 carbon atoms, or N-alkyl-N-alkoxyalkylcarbamoyl in which the alkyl group contains 2 to 4 carbon atoms and the alkoxyalkyl group contains 3 to 4 carbon atoms.

Preferably, $R^3$ is alkyl containing 1–4 carbon atoms, allyl, 2-methylallyl, alkoxyalkyl containing 3 or 4 carbon atoms, phenyl containing a single halosubstituent and $R^4$ is alkyl containing 1–8 carbon atoms, allyl, methylallyl or alkoxyalkyl containing 3–8 carbon atoms. It is preferred that the sulphamoyl group is dialkylsulphamoyl in wich the alkyl groups are the same or different and each contain 1–4 carbon atoms, diallylsulphamoyl, di-(2-methylallyl)sulphamoyl, or N-allyl-N-alkylsulphamoyl in which the alkyl group contains 1–4 carbon atoms. Especially suitable compounds of formula II are those in which:
(a) the carbamoyl group is diallylcarbamoyl and 177°-sulphamoyl group is dialkylsulphamoyl, di(2-methylallyl)sulphamoyl or N-allyl-N-alkylsulphamoyl,
(b) the carbamoyl group is dialkylcarbamoyl and the sulphamoyl group is dialkylsulphamoyl, diallylsulphamoyl or N-allyl-N-alkylsulphamoyl,
(c) the carbamoyl group is N-allyl-N-alkylcarbamoyl and the sulphamoyl group is dialkylsulphamoyl, diallysulphamoyl or N-allyl-N-alkylsulphamoyl,
(d) the carbamoyl group is N-alkyl-N-alkoxyalkylcarbamoyl and the sulphamoyl group is dialkylsulphamoyl, diallylsulphamoyl or N-allyl-N-alkylsulphamoyl.

The present invention also provides herbicidal compositions which comprise as an active ingredient a compound of the general formula III is association with a diluent or carrier. The diluent or carrier may be a solid or liquid, optionally in association with a surface-active agent, for example a dispersing agent, emulsifying agent or wetting agent.

According to a further feature of the present invention there is provided a method for the pre-weed emergence control of graminaceous weeds which comprise applying to the locus of the weeds for example the soil, a compound of the general formula III. A particular embodiment of this feature is a method for the selective pre-weed emergence control of graminaceous weeds such as barnyard grass, crabgrass, yellow foxtail and Johnson grass in crop area which comprises applying to the crop area a compound for the general formula III at an application rate sufficient to control the weeds but substantially non-phytotoxic to the crop.

We have found that the triazole compounds of formulae I, II and III have valuable herbicidal properties against graminaceous weeds. For example, the compoounds possess a high level of pre-weed emergence herbicidal activity against the graminaceous weeds crabgrass (*Digitari sanguinalis*), barnyard grass (*Echinochloa crusgalli*), yellow foxtail (*Setaria lutescens*) and Johnson grass (*Sorgham halepense*). Furthermore, detailed trails in the glasshouse have shown that the compounds give a pre-weed emergence control of each of these weeds at application rates that cause no significant phytotoxic effect on the crops cotton, soyabean, peanut and maize when the compounds are applied prior to the emergence of these crops. Accordingly the compounds of the present invention can be used for the selective pre-emergence control of all of these weeds in these crops. This is an important advantage, since crabgrass, barnyard grass, yellow foxtail and Johnson grass are all important weeds in cotton, soyabean, peanut and maize and often occur together in these crops.

We have found that the compounds of the present invention have superior herbicidal properties to a variety of closely related 1,2,4-triazoles within the hereinbefore defined broad group of compounds described in U.S. Pat. Specification No. 3,308,131, including a representative selection of the compounds specifically exemplified in that patent specification.

Detailed trails in the glasshouse have demonstrated that, in contrast to the compounds of the present invention, these closely related compounds do not possess both the above-described high level of pre-weed emergence herbicidal activity and the above-described ability to control selectively all four of the weeds crabgrass, barnyard grass, yellow foxtail and Johnson grass in cotton, soyabean, peanut and maize.

The compositions of the present invention include not only compositions in a suitable form for application but alo concentrated primary compositions which may be supplied to the user and which require dilution with a suitable quantity of wwater or other diluent before application.

Typical compositions falling within the present invention include the following:

(a) Dispersions and dispersible preparations

As dispersions, the compositions comprise essentially a triazole compound of the general formula I, II or III ispersed in an aqueous medium. It is convenient to supply the consumer with a primary composition which may be diluted with water to form a dispersion having the desired concentration; the primary composition may be in any one of the following forms. It may be provided as a dispersible solution which comprises a compound of the general formula I, II or III dissolved in a water-miscible solvent with the addition of a dispersing agent. Alternatively it may be provided as a dispersible powder which comprises a compound of the general formula I, II or III and a dispersing agent. A further alternative comprises a compound of the general formula I, II or III in the form of a finely ground powder in association with a dispersing agent and intimately mixed with water to give a paste or cream. This paste or cream may if desired be added to an emulsion of oil in water to give a dispersion of active ingredient in an aqueous oil emulsion.

(b) Emulsions and emulsifiable preparations

Emulsions comprise essentially a triasole compound of the general formula I, II or III dissolved in a water-immiscible solvent which is formed into an emulsion with water in the presence of an emulsifying agent. An emulsion of the desired concentration may be formed from a primary composition of the following types. A concentrated stock emulsion may be supplied comprising a compound of the general formula I, II or III in combination with an emulsifying agent, water and a water-immiscible solvent. Alternatively there may be supplied an emulsifiable concentrate comprising a solution of a compound of the general formula I, II or III in a water-immiscible solvent containing an emulsifying agent.

(c) Dusting powders

A dusting powder comprises a triazole compound of the general formula I, II or III intimately mixed and ground with a solid pulverulent diluent, for example kaolin.

(d) Granular solids

These may comprise a compound of the general formula I, II or III associated with similar diluents to those which may be employed in dusting powders, but the mixture is granulated by known methods. Alternatively they may comprise the active eingredient absorbed or adsorbed on a pre-formed granular diluent for example fullers earth, attapulgite and limestone grit.

In addition to the ingredients already mentioned, the compositions of the invention may also contain other substances conventionally used in the art, the function of which may be to improve the ease of handling of the compositions or to improve their utility. For example an inert diluent such as kaolin may be included in dispersible powders in order to facilitate grinding and to provide sufficient bulk for mixing with water. As a further example, the compositions intended for dilution with water prior to application may also contain a wetting agent in order to obtain rapid wetting-out of the materials and to ensure satisfactory coverage of the soil. Also when dusts are prepared, a lubricant such as magnesium stearate may be added to the mixture to promote both easier mixing of the components and to ensure that the final product has free-flowing properties.

The compositions hereinbefore described wherein the active ingredients are present in solid form, for example dusting powders and dispersible powders, should preferably contain the compound of the general formula I, II or III in the form of very fine particles; the majority of the particles, of the order of at least 95% should be less than 50 $\mu$, with about 75% of them being 5-20 $\mu$. The adjuvants conventionally used in such compositions are generally of this particle size or smaller. The compositions can be prepared by means of conventional grinding equipment such as a hammer mill.

The concentration of compound of the general formula I, II or III in the primary compositions which may be provided for the preparation of any of the forms in which the compositions of the invention may be used may vary widely and may be, for example, 2-95% w/w of the composition. It will be appreciated that this concentration will be influenced by the nature of the primary composition and the physical properties of its ingredients.

The concentration of the compound of general formula I, II or III in the compositions for application to control weeds should be at least 0.001% w/w, preferably 0.05-10% w/w.

In addition to a compound of the general formula I, II or III, the compositions of the present invention may contain one or more additional active ingredients, for example one or more insecticides, nematocides, or additional herbicides. Such an additional herbicide may be, for example, a substituted urea, for example diuron or monuron; a triazine, for example simazine or atrazine; a substituted acetanilide, for example propachlor; a nitrophenyl ether, for example nitrofen; a carbamate, for example chlorpropham; or a thiolcarbamate, for example, EPTC or tri-allate.

The invention includes a method for the pre-weed emergence control of graminaceous weeds which comprises applying to the locus of the weeds, for example the soil, a triazole compound of the formula I, II or III. This method may be used subsequent to the emergence of the crop, for example for the pre-weed emergence control of graminaceous weeds such as barnyard grass in seeded or transplanted rice, but is often used prior to the emergence of the crop, as is usually the case with the control of crabgrass, barnyard grass, yellow foxtail and Johnson grass in cotton, soyabean, peanut and maize. When the method is used prior to the emergence of the crop, it is convenient to apply the compounds of the invention to the soil in which the crop is sown at or just prior to the time of sowing. Thus, for example, the compounds of the invention may be incorporated into the top layer of soil as part of a sowing procedure.

For the control of graminaceous weeds, the compounds of the invention are generally used at an application rate of 0.05-50 lb./acre, preferably 0.1-20 lb./acre. Selective pre-weed emergence control of weeds may be achieved in many instances at an application rate within the range 0.1-10 lb./acre.

The selective pre-weed emergence herbicidal activity of the compounds of the present invention is demonstrated by the results obtained in detailed trials carried out in the glasshouse. In these trials, trays of soil were sown with seeds of various weeds and crops, and then immediately sprayed with aqueous suspensions of the compounds under test at logarithmically reducing application rates of test compound within the range 8-1/32 lb./acre. Seeded trays of soil receiving no chemical treatment were used as controls. The weeds were crabgrass (CG), barnyard grass (BG), yellow foxtail (YF) and Johnson grass (JG). The crops used were cotton (CO), soyabean (SB), maize (M) and peanut (P).

In the case of the weeds, the minimum application rate was recorded at which control of the weeds was achieved, as shown by emergent seedlings that were severely and irrecoverably stunted. In the case of the crops, the minimum application rate was recorded at which a phytotoxic effect was observed on the emergent seedlings. In some cases no phytotoxic effect was observed at the maximum application rate of test compound of 8 lb./acre, and this result was recorded as ">8". The results obtained with various compounds within general formula III are shown in the following Table. In this Table the following abbreviations are used:

Me=methyl, Et=ethyl, Pr=propyl, Bu=butyl, Pen=pentyl, Hex=hexyl, i=iso and s=secondary. Alkyl radicals without the designation i- or s- signify normal radicals.

Table 1

| Compound III | | Minimum rate (lb./acre) | | | | | | | |
|---|---|---|---|---|---|---|---|---|---|
| | | Control | | | | | Phytotoxicity | | |
| $SO_2NR^3R^4$ | $CONR^1R^2$ | CC | BG | YP | JC | N | CO | SB | P |
| NMe$_2$ | N(allyl)$_2$ | 1/4 | 1/4 | 1/8 | 1/4 | 2 | 2 | 4 | >8 |

Table 1-continued

| Compound III | | Minimum rate (lb./acre) | | | | | | | |
|---|---|---|---|---|---|---|---|---|---|
| | | Control | | | | Phytotoxicity | | | |
| $SO_2NR^3R^4$ | $CONR^1R^2$ | CC | BG | YP | JC | N | CO | SB | P |
| N(Bu)Me | " | 1/16 | 1/16 | 1/8 | 1/16 | 4 | >8 | >8 | >8 |
| N(s-Bu)Me | " | 1/32 | 1/32 | 1/8 | 1/32 | 1/2 | >8 | >8 | >8 |
| N(Me)(cyclohexyl) | " | 1/4 | 1/4 | 1/4 | 1/2 | 2 | >8 | >8 | >8 |
| N(allyl)Me | " | 1/16 | 1/32 | 1/8 | 1/16 | 2 | >8 | >8 | >8 |
| $NEt_2$ | " | 1/32 | 1/32 | 1/32 | 1/32 | 2 | 4 | 4 | >8 |
| N(Et)Hex | " | 1/4 | 1/4 | 1/8 | 1/4 | 2 | >8 | >8 | >8 |
| $NPr_2$ | " | 1/4 | 1/4 | 1/4 | 1/16 | 4 | >8 | 4 | >8 |
| N(i-Pr)Pr | " | 1/16 | 1/32 | 1/8 | 1/4 | 2 | >8 | >8 | >8 |
| N(Pr)Bu | " | 1/8 | 1/2 | 1/2 | 1/2 | 2 | 2 | 2 | 4 |
| $NBu_2$ | " | 1/8 | 1/2 | 1/4 | 1/8 | 4 | 4 | >8 | >8 |
| $N(allyl)_2$ | " | 1/4 | 1/8 | 1/8 | 1/16 | 2 | 4 | 4 | 4 |
| $N(Me-allyl)_2$ | " | 1/16 | 1/16 | 1/4 | 1/2 | >8 | >8 | >8 | >8 |
| pyrrolidino | " | 1/8 | 1/8 | 1/8 | 1/16 | 4 | 2 | 4 | >8 |
| piperidyl | " | 1/8 | 1/8 | 1/16 | 1/2 | 4 | 2 | 4 | 4 |
| morpholino | " | 1/2 | 1/2 | 1/4 | 1/4 | 4 | >8 | 4 | >8 |
| 2,6-dimethyl-morpholino | " | 1/8 | 1/4 | 1/8 | 1/8 | >8 | 4 | >8 | 4 |
| 4-methyl-piperidino | " | 1/8 | 1/8 | 1/8 | 1/8 | >8 | >8 | >8 | >8 |
| hexamethylene-imino | " | 1/4 | 1/4 | 1/4 | 1/4 | >8 | >8 | >8 | >8 |
| heptamethylene-imino | " | 1/4 | 1/8 | 1/4 | 1/4 | >8 | >8 | >8 | >8 |
| $NMe_2$ | $NEt_2$ | 1/4 | 1/2 | 1/8 | 1/2 | 2 | 4 | 4 | >8 |
| $NEt_2$ | " | 1/16 | 1/8 | 1 | 1/2 | 4 | >8 | >8 | >8 |
| $N(allyl)_2$ | " | 1/16 | 1/16 | 1/32 | 1/32 | 1/2 | >8 | >8 | >8 |
| N(Me)Bu | " | 1/32 | 1/4 | 1/8 | 1/4 | 2 | >8 | >8 | >8 |
| N(s-Bu)Me | " | 1/8 | 1/32 | 1/32 | 1/4 | 1 | 4 | 4 | >8 |
| N(Me)(cyclohexyl) | " | 1 | 1/4 | 1/2 | 1/2 | 4 | >8 | >8 | >8 |
| N(allyl)Me | " | 1/16 | 1/4 | 1/4 | 1/4 | 2 | 4 | >8 | >8 |
| piperidyl | " | 1/8 | 1/8 | 1/32 | 1/4 | 1 | >8 | >8 | >8 |
| morpholino | " | 1/16 | 1/4 | 1/8 | 1/16 | 1 | 1 | 2 | >8 |
| 2,6-dimethyl-morpholino | " | 1/32 | 1/4 | 1/8 | 1/4 | 1 | 4 | 4 | >8 |
| pyrrolidino | n(Me)Et | 1/32 | 1/16 | 1/32 | 1/32 | 1 | 1 | 2 | 2 |
| pyrrolidino | N(Me)Bu | 1/4 | 1/4 | 1/4 | 1/4 | 1 | 2 | 4 | 8 |
| N(Me)Bu | N(Me)(cyclohexyl) | 1/4 | 1/2 | 1/4 | 1/4 | 2 | >8 | >8 | >8 |
| N(allyl)Me | " | 1/16 | 1/4 | 1/2 | 1/2 | 4 | >8 | 4 | >8 |
| $NEt_2$ | " | 1/16 | 1/16 | 1/8 | 1/2 | 4 | >8 | 4 | >8 |
| $N(allyl)_2$ | " | 1/8 | 1/4 | 1/2 | 1/4 | 2 | >8 | >8 | >8 |
| pyrrolidino | " | 1/4 | 1/4 | 1/8 | 1/4 | 4 | 4 | >8 | 4 |
| $NEt_2$ | N(Et)Bu | 1/16 | 1/8 | 1/8 | 1/8 | 4 | 4 | >8 | >8 |
| N(Me)Bu | " | 1/2 | 1/2 | 1/2 | 1/4 | 2 | >8 | 4 | >8 |
| N(allyl)Me | " | 1/32 | 1/32 | 1/32 | 1/32 | >8 | >8 | 4 | >8 |
| piperidyl | " | 1/4 | 1/4 | 1/4 | 1/4 | 2 | >8 | >8 | >8 |
| N(allyl)Me | N(allyl)Et | 1/32 | 1/32 | 1/32 | 1/8 | 2 | >8 | 2 | >8 |
| $NEt_2$ | N(allyl)Et | 1/8 | 1/4 | 1/8 | 1/16 | 1 | 2 | 2 | 2 |
| $N(allyl)_2$ | N(Et)Bu | 1/32 | 1/32 | 1/16 | 1/32 | 4 | >8 | >8 | >8 |
| $N(allyl)_2$ | N(allyl)Et | 1/16 | 1/16 | 1/8 | 1/8 | 4 | >8 | 4 | >8 |
| pyrrolidino | " | 1/16 | 1/16 | 1/16 | 1/16 | 1/4 | 4 | 2 | >8 |
| piperidyl | " | 1/16 | 1/16 | 1/16 | 1/16 | 1/2 | >8 | >8 | >8 |
| N(Me)Bu | N(allyl)Pr | 1/16 | 1/16 | 1/32 | 1/16 | 2 | >8 | >8 | >8 |
| N(allyl)Me | " | 1/16 | 1/16 | 1/4 | 1/16 | 2 | >8 | >8 | >8 |
| $NEt_2$ | " | 1/16 | 1/16 | 1/16 | 1/16 | 1 | >8 | 4 | >8 |
| $N(allyl)_2$ | " | 1/16 | 1/8 | 1/8 | 1/4 | 2 | >8 | >8 | >8 |
| $N(allyl)_2$ | N(Pr)(prop-2-ynyl) | 1/16 | 1/4 | 1/4 | 1/8 | >8 | 4 | >8 | 4 |
| N(Me)Bu | " | 1/4 | 1/4 | 1/16 | 1/16 | >8 | >8 | >8 | >8 |
| N(allyl)Me | " | 1/16 | 1/8 | 1/2 | 1/16 | >8 | 4 | 4 | >8 |
| pyrrolidine | N(allyl)Pr | 1/16 | 1/8 | 1/16 | 1/4 | 2 | >8 | 4 | >8 |
| piperidyl | " | 1/16 | 1/8 | 1/16 | 1/8 | 4 | 4 | >8 | >8 |
| piperdyl | N(Pr)(prop-2-ynyl) | 1/8 | 1/4 | 1/8 | 1/8 | >8 | 2 | 4 | >8 |

Table 1-continued

| Compound III | | Minimum rate (lb./acre) | | | | | | | |
|---|---|---|---|---|---|---|---|---|---|
| | | Control | | | | Phytotoxicity | | | |
| SO$_2$NR$^3$R$^4$ | CONR$^1$R$^2$ | CC | BG | YP | JC | N | CO | SB | P |
| N(Et)Bu | N(allyl)$_2$ | 1/8 | 1/16 | 1/4 | 1/8 | 4 | >8 | >8 | >8 |
| N(allyl)Hex | " | 1/4 | 1/2 | 1/2 | 1/2 | 2 | 4 | >8 | >8 |
| N(allyl)$_2$ | N(2-methyl allyl)$_2$ | 1/8 | 1/8 | 1/8 | 1/4 | >8 | >8 | >8 | >8 |
| NBu$_2$ | NEt$_2$ | 1/4 | 1/4 | 1/4 | 1/4 | 2 | >8 | 4 | >8 |
| N(allyl)Pr | " | 1/16 | 1/8 | 1/16 | 1/8 | 1 | 4 | 4 | >8 |
| N(Me)Pen | " | 1/2 | 1/4 | 1/4 | 1/2 | 2 | >8 | >8 | >8 |
| N(CH$_2$CH$_2$OEt)$_2$ | " | 1/4 | 1/4 | 1/4 | 1/4 | 1 | >8 | 2 | >8 |
| N(Me)Hex | " | 1/8 | 1/4 | 1/8 | 1/4 | 4 | >8 | >8 | >8 |
| N(Et)Pen | " | 1/16 | 1/16 | 1/8 | 1/8 | 2 | >8 | 4 | >8 |
| N(allyl)Et | " | 1/8 | 1/16 | 1/16 | 1/16 | 4 | 4 | >8 | >8 |
| N(Pr)Hex | " | 1/2 | 1/2 | 1/2 | 1/2 | 4 | 4 | >8 | >8 |
| N(Bu)Et | " | 1/16 | 1/16 | 1/16 | 1/16 | 1/2 | >8 | 2 | >8 |
| NEt$_2$ | N(Me)Bu | 1/8 | 1/16 | 1/16 | 1/16 | 1 | 4 | 2 | >8 |
| N(allyl)$_2$ | " | 1/16 | 1/16 | 1/16 | 1/16 | 1 | 4 | 1 | >8 |
| N(Me)Et | N(allyl)$_2$ | 1/16 | 1/16 | 1/16 | 1/16 | 1/2 | 2 | 1 | >8 |
| N(Me)Pen | " | 1/8 | 1/8 | 1/4 | 1/4 | >8 | >8 | >8 | >8 |
| N(Me)Hex | " | 1/16 | 1/8 | 1/16 | 1/16 | 4 | >8 | >8 | >8 |
| N(Et)Pen | " | 1/8 | 1/16 | 1/8 | 1/16 | >8 | >8 | >8 | >8 |
| N(Et)(cyclopropyl) | " | 1/4 / 1/4 | 1/4 | 1/4 | 4 | 2 | 1 | 2 | |
| N(allyl)Et | " | 1/16 | 1/8 | 1/8 | 1/8 | >8 | >8 | >8 | >8 |
| N(Et)(2-allyloxyethyl) | " | 1/4 | 1/4 | 1/4 | 1/4 | 4 | 1 | >8 | >8 |
| N(Et)(2-chloroallyl) | " | 1/4 | 1/4 | 1/4 | 1/4 | >8 | 4 | 4 | >8 |
| N(allyl)Pr | " | 1/16 | 1/8 | 1/8 | 1/8 | 4 | 4 | >8 | >8 |
| N(Pr)(prop-2-ynyl) | " | 1/8 | 1/16 | 1/8 | 1/8 | 4 | >8 | >8 | >8 |
| N(Pr)(CH$_2$)$_2$OMe | " | 1/4 | 1/2 | 1/4 | 1/2 | >8 | 4 | 4 | >8 |
| N(Pr)CH$_2$CH$_2$Cl | " | 1/16 | 1/4 | 1/16 | 1/4 | >8 | >8 | >8 | >8 |
| N(Pr)(2-chloroallyl) | " | 1/4 | 1/8 | 1/8 | 1/8 | >8 | 4 | 4 | >8 |
| N(Me)Bu | N(Me)Hex | 1/4 | 1/2 | 1/4 | 1/4 | >8 | >8 | >8 | >8 |
| piperidyl | N(Et)s-Bu | 1/16 | 1/8 | 1/16 | 1/16 | 4 | >8 | 4 | >8 |
| N(allyl)$_2$ | " | 1/4 | 1/8 | 1/4 | 1/4 | 1 | 4 | 4 | >8 |
| N(s-Bu)Me | N(Et)Bu | 1/4 | 1/4 | 1/4 | 1/4 | >8 | >8 | >8 | >8 |
| N(allyl)Pr | N(allyl)Et | 1/16 | 1/16 | 1/16 | 1/16 | 1 | >8 | 4 | >8 |
| NEt$_2$ | N(Hex)Et | 1/4 | 1/4 | 1/4 | 1/4 | 4 | >8 | >8 | >8 |
| NEt$_2$ | N(Et)(cyclopropyl) | 1/4 | 1/4 | 1/4 | 1/4 | 2 | 2 | 1 | 8 |
| NMe$_2$ | N(allyl)Et | 1/8 | 1/16 | 1/16 | 1/16 | 1/2 | 2 | 4 | 4 |
| NEt$_2$ | N(i-Bu)Et | 1/4 | 1/4 | 1/4 | 1/4 | 2 | >8 | >8 | >8 |
| N(Me)Bu | N(Pr)(CH$_2$)$_2$OEt | 1 | 1/2 | 1/2 | 1/2 | >8 | >8 | >8 | >8 |
| N(Me)Bu | N(allyl)Pr | 1/16 | 1/16 | 1/16 | 1/16 | 1/2 | 4 | 1 | >8 |
| N8Et)Bu | N(allyl)Pr | 1/16 | 1/16 | 1/16 | 1/16 | 2 | 2 | 2 | >8 |
| N(Me)s-Bu | " | 1/4 | 1/4 | 1/4 | 1/2 | 4 | 4 | 4 | >8 |

Table 1-continued

| Compound III | | Minimum rate (lb./acre) | | | | | | | |
|---|---|---|---|---|---|---|---|---|---|
| | | Control | | | | Phytotoxicity | | | |
| $SO_2NR^3R^4$ | $CONR^1R^2$ | CC | BG | YP | JC | N | CO | SB | P |
| $NEt_2$ | Pr, prop-2-ynyl (N) | 1/8 | 1/4 | 1/8 | 1/2 | 4 | 4 | 4 | >8 |
| $NEt_2$ | Pr, $CH_2CH_2Cl$ (N) | 1/2 | 1/2 | 1/2 | 1/4 | >8 | >8 | >8 | >8 |
| $N(allyl)_2$ | Et, 2-chloroallyl (N) | 1/16 | 1/8 | 1/8 | 1/2 | >8 | >8 | >8 | >8 |
| $NEt_2$ | Et, 2-allyloxyethyl (N) | 1/2 | 1/2 | 1/4 | 1/2 | >8 | >8 | >8 | |
| $NEt_2$ | Pr, $CH_2OMe$ (N) | 1/8 | 1/8 | 1/8 | 1/8 | >8 | >8 | >8 | >8 |
| $NEt_2$ | Pr, $(CH_2)_2OMe$ (N) | 1/8 | 1/8 | 1/4 | 1/16 | 2 | >8 | >8 | >8 |
| $NEt_2$ | Et, $(CH_2)_3OMe$ (N) | 1/8 | 1/8 | 1/4 | 1/4 | 2 | >8 | >8 | >8 |
| $NEt_2$ | Et, $(CH_2)_2OEt$ (N) | 1/4 | 1/8 | 1/2 | 1/2 | >8 | >8 | >8 | >8 |
| $N(allyl)_2$ | Et, $(CH_2)_2OEt$ (N) | 1/8 | 1/4 | 1/2 | 1/4 | 4 | >8 | 4 | >8 |
| $N(allyl)_2$ | Et, $(CH_2)_3OMe$ (N) | 1/16 | 1/4 | 1/8 | 1/8 | 2 | 2 | >8 | >8 |
| $NEt_2$ | Et, $CH_2CH_2Cl$ (N) | 1/4 | 1/4 | 1/4 | 1/4 | 1 | >8 | 1 | >8 |
| $NEt_2$ | Et, 2-chloroallyl (N) | 1/8 | 1/4 | 1/8 | 1/4 | >8 | >8 | >8 | >8 |
| $NEt_2$ | N(allyl)Pen | 1/8 | 1/8 | 1/8 | 1/8 | 4 | >8 | >8 | >8 |
| $N(allyl)_2$ | N(allyl)Pen | 1/16 | 1/8 | 1/16 | 1/4 | >8 | >8 | >8 | '8 |
| $N(allyl)_2$ | N(Me)Et | 1/16 | 1/16 | 1/8 | 1/16 | 1 | 2 | 2 | >8 |
| pyrrolidino | " | 1/32 | 1/16 | 1/32 | 1/32 | 1 | 1 | 2 | 2 |
| $N(allyl)_2$ | N(allyl)Me | 1/16 | 1/16 | 1/16 | 1 | 2 | 4 | >8 | |
| $NEt_2$ | " | 1/8 | 1/16 | 1/16 | 1/8 | 1/2 | 2 | 1 | >8 |
| N(Me)Bu | " | 1/16 | 1/16 | 1/16 | 1/16 | 2 | 2 | 4 | >8 |
| $NEt_2$ | N(i-Pr)Et | 1/16 | 1/16 | 1/16 | 1/16 | 1 | >8 | 2 | >8 |
| N(allyl)Hex | N(Pr)Et | 1/2 | 1/2 | 1/2 | >8 | >8 | >8 | >8 | |
| N(Et)Bu | N(i-Pr)Et | 1/16 | 1/16 | 1/16 | 1/16 | 1 | >8 | 1 | >8 |
| $N(allyl)_2$ | " | 1/16 | 1/16 | 1/16 | 1/16 | 1 | >8 | 2 | >8 |
| $NEt_2$ | N(Et)Bu | 1/8 | 1/8 | 1/8 | 1/4 | >8 | >8 | >8 | >8 |
| $N(allyl)_2$ | Et, prop-2-ynyl (N) | 1/4 | 1/2 | 1/8 | 1/8 | >8 | >8 | >8 | >8 |
| $NEt_2$ | " | 1/8 | 1/4 | 1/8 | 1/4 | >8 | >8 | >8 | >8 |
| N(Me)Bu | " | 1/8 | 1/4 | 1/4 | 1/4 | 2 | >8 | 4 | >8 |
| N(Bu)Me | N(Et)s-Bu | 1/8 | 1/8 | 1/8 | 1/8 | >8 | >8 | >8 | 2 |

Table 1-continued

| Compound III | | Minimum rate (lb./acre) | | | | | | | |
|---|---|---|---|---|---|---|---|---|---|
| | | Control | | | | Phytotoxicity | | | |
| $SO_2NR^3R^4$ | $CONR^1R^2$ | CC | BG | YP | JC | N | CO | SB | P |
| N(allyl)$_2$ | " | 1/16 | 1/16 | 1/16 | 1/16 | 4 | >8 | 4 | >8 |
| N(Me)Bu | N(Pr)(CH$_2$)$_2$OMe | 1/16 | 1/16 | 1/16 | 1/16 | 1 | 4 | 4 | 1 |
| piperidyl | N(Pr)(CH$_2$)$_2$OMe | 1/16 | 1/16 | 1/16 | 1/16 | >8 | >8 | 4 | >8 |
| NEt$_2$ | N(Pr)(CH$_2$)$_2$OEt | 1/2 | 1/4 | 1/2 | 1/2 | >8 | >8 | >8 | >8 |
| N(Me)Bu | N(Et)(CH$_2$)$_2$OEt | 1/4 | 1/2 | 1/2 | 1/2 | 4 | >8 | >8 | >8 |
| NEt$_2$ | N(Et)Pen | 1/4Z | 1/8 | 1/16 | 1/16 | 4 | >8 | >8 | >8 |
| N(allyl)$_2$ | " | 1/8 | 1/4 | 1/16 | 1/8 | 4 | >8 | >8 | >8 |
| N(allyl)$_2$ | N(Pr)(2-chloroallyl) | 1 | 1/4 | 1/2 | 1/4 | >8 | >8 | >8 | >8 |
| NEt$_2$ | N(allyl)i-Pr | 1/4 | 1/4 | 1/4 | 1/4 | 1 | >8 | >8 | >8 |
| N(allyl)$_2$ | " | 1/16 | 1/4 | 1/4 | 1/4 | 1 | >8 | 4 | >8 |
| N(allyl)Me | N(Pr)(2-chloroallyl) | 1 | 1/4 | 1/2 | 1/2 | >8 | >8 | >8 | >8 |
| NEt$_2$ | N(allyl)Bu | 1/2 | 1/2 | 1/4 | 1/4 | 2 | >8 | 4 | >8 |
| NEt$_2$ | N(allyl)Hex | 1 | 1/2 | 1/4 | 1/4 | >8 | >8 | >8 | >8 |
| NMe$_2$ | N(allyl)i-Bu | 1/16 | 1/16 | 1/16 | 1/16 | 1 | >8 | 2 | >8 |
| NEt$_2$ | 1/4 | 1/4 | 1/4 | 1/4 | 1 | 4 | >8 | >8 | |
| piperidyl | N(Me)Hex | 1/4 | 1/4 | 1/4 | 1/4 | 4 | 4 | 2 | >8 |
| N(Me)(4-fluorophenyl) | N(allyl)$_2$ | 1/16 | 1/16 | 1/8 | 1/8 | >8 | >8 | >8 | >8 |
| N(Me)(4-chlorophenyl) | " | 1/4 | 1/16 | 1/4 | 1/4 | 4 | >8 | 4 | >8 |
| N(Me)(4-bromophenyl) | " | 1/8 | 1/8 | 1/2 | 1 | >8 | >8 | >8 | >8 |
| N(Me)(4-bromophenyl) | NEt$_2$ | 1/16 | 1/4 | 1/4 | 1/8 | 2 | >8 | 4 | >8 |
| N(Me)(4-chlorophenyl) | " | 1/16 | 1/16 | 1/32 | 1/16 | 1 | >8 | 4 | >8 |
| N(Me)(4-flu) | " | 1/16 | 1/16 | 1/8 | 1/32 | 2 | >8 | >8 | >8 |
| N(Me)(4-flu) | N(Me)Bu | 1/16 | 1/16 | 1/4 | 1/16 | >8 | >8 | 2 | >8 |
| " | N(Me)Hex | 1/4 | 1/4 | 1/2 | 1/4 | >8 | >8 | >8 | >8 |
| " | N(Me)(cyclohexyl) | 1/16 | 1/16 | 1/16 | 1/16 | >8 | 4 | >8 | >8 |
| " | N(Et)Bu | 1/16 | 1/16 | 1/16 | 1/16 | 4 | >8 | >8 | >8 |

Table 1-continued

| Compound III | | Minimum rate (lb./acre) | | | | | | | |
|---|---|---|---|---|---|---|---|---|---|
| | | Control | | | | Phytotoxicity | | | |
| $SO_2NR^3R^4$ | $CONR^1R^2$ | CC | BG | YP | JC | N | CO | SB | P |
| " | N(allyl)Et | 1/4 | 1/4 | 1/4 | 1/4 | 2 | 4 | 4 | >8 |
| " | N(allyl)Br | 1/16 | 1/16 | 1/16 | 1/16 | >8 | >8 | >8 | >8 |
| N(Me)(4-fluorophenyl) | N(Et)(2-chloroallyl) | 1/8 | 1/16 | 1/8 | 1/16 | >8 | >8 | 4 | >8 |
| " | N(allyl)Me | 1/8 | 1/16 | 1/8 | 1/8 | 2 | 4 | >8 | >8 |
| " | N(Pr)Et | 1/16 | 1/16 | 1/16 | 1/16 | 1 | >8 | 2 | >8 |
| " | N(Et)(allyl) | 1/4 | 1/4 | 1/4 | 1/4 | >8 | >8 | >8 | >8 |
| " | N(Et)Bu | 1/8 | 1/8 | 1/16 | 1/16 | 2 | >8 | 4 | >8 |
| " | N(Pr)((CH$_2$)$_2$OMe) | 1/16 | 1/16 | 1/16 | 1/16 | 1/4 | >8 | >8 | >8 |
| " | N(Et)Pen | 1/8 | 1/4 | 1/4 | 1/8 | >8 | >8 | 4 | >8 |
| " | N(allyl)i-Bu | 1/16 | 1/16 | 1/16 | 1/16 | 4 | 2 | 2 | >8 |

For purposes of comparison, various 1,2,4-triazoles within the scope of the isomeric formulae A but outside the scope of the formula, I, II and III (compounds of the formula III are wholly outside the scope of formulae A), were included in the glasshouse trials described above, using application rates logarithmically reducing from 32 lb./acre. The results obtained are given in the following Tables 2 and 3, in which " " designates a compound that is specifically exemplified in U.S. Pat. Specification No. 3,308,131. The compounds that gave no control of any of the weeds crabgrass, barnyard grass, yellow foxtail and Johnson grass at the maximum application rate of 32 lb./acre are listed in Table 3. In view of their lack of activity against the weeds, these components were not included in the crop tests. Of the compounds listed in TAble 3, those that are believed to have been obtained as a mixture of isomers (corresponding to formulae A) containing appreciably more than 10% of each isomer, or those in which the isomeric structure is uncertain, are designated 1(2)- in the nomenclature of the carbamoyl group. The remaining compounds are believed to have been obtained substantially as the isomer given, predominantly as this isomer with less than 10% of the other isomer.

Table 2

| Compound (I, X=O, $R^8$=M) | | Minimum rate (lb./acre) | | | | | | | |
|---|---|---|---|---|---|---|---|---|---|
| | | control | | | | phytotoxicity | | | |
| $R^7$ | $NR^5R^6$ | CG | BG | YF | JG | CO | GB | N | F |
| Mo | NMe$_2$ | 1 | 16 | 2 | 2 | 4 | 8 | 4 | 8 |
| Cl | " | 4 | 2 | 2 | 2 | 2 | 4 | 2 | 4 |
| Br | " | 4 | 4 | 32 | 4 | 1 | 1 | 2 | 4 |
| SMe | " | 1 | 4 | 4 | 2 | ½ | 2 | 2 | 2 |

TABLE 3

Compounds with the following substituents on the 1,2,4-triazole ring gave no weed control at 32 lb./acre.

1-dimethylcarbamoyl
1-dimethylthiocarbamoyl
1(2)-dimethylthiocarbamoyl-3-ethylthio
1(2)-diethylthiocarbamoyl-3-ethylthio
1(2)-dimethylthiocarbamoyl-3-methylthio-5-methyl
1(2)-dimethylcarbamoyl-3-methylsulphonyl-5-methyl
1(2)-diethylcarbamoyl-3-methylthio-5-methyl
1(2)-N-methyl-N-n-butylcarbazoyl-3-methylthio-5-methyl
1(2)-dimethylcarbamoyl-3-ethylthio-5-methyl
1-dimethylcarbamoyl-3-dodecylthio-5-methyl
1-dimethylcarbamoyl-3-n-hexylthio
1-dimethylcarbamoyl-3-cyclohexylthio
1-dimethylcarbamoyl-3-dodecylthio
1-dimethylcarbamoyl-3-undecyl-5-methylthio
1-dimethylcarbamoyl-3-benzyl
1-dimethylcarbamoyl-3-benzylthio-5-methyl
1-dimethylcarbamoyl-3-phenyl-5-methylthio
1-dimethylcarbamoyl-3p-nitrophenylthio-5-methyl
1-dimethylcarbamoyl-3-(2,4-dinitrophenylthio)
1-dimethylcarbamoyl-3,5-dimethyl
1-dimethylcarbamoyl-3(2-diethylaminoethylthio)-5-methyl Table 3 (continued) substituents on 1,2,4-triazole ring 1-dimethylcarbamoyl-3-ethoxycarbonylmethylthio-5-methyl
1-dimethylcarbamoyl-3-(1-dimethylcarbamoyl-1,2,4-triazole-3-yldithio)
1-(4-methylpiperidinocarbonyl)
1(2)-pyrrolidinocarbonyl-3-methylthio-5-methyl
1-piperidinocarbonyl-3-ethylthic
1(2)-(4-methylpiperazinocarbonyl)-3-ethylthio
1-(1,2,3,4-tetrahydroquinolinocarbonyl)-3-ethylthio
1(2)-(N-methyl-N-methoxycarbamoyl)-3-ethylthio
1-diallylcarbamoyl
1(2)-diallylcarbamoyl-3-ethylthio-5-methyl
1-diallylcarbamoyl-3-(2-diethylaminoethylthio)
1-diallylcarbamoyl-3-methoxycarbonylmethyl
1-di(cyanomethyl)carbamoyl-3-ethylthio The results given above show that the compounds listed in Table 1 are markedly superior to the compounds listed in Tables 2 and 3 in respect of their high level of selective pre-emergence activity against all four of the weeds crabgrass, barnyard grass, yellow foxtail and Johnson grass in the crops cotton, soyabean, maize and peanut.

It can be seen from the foregoing description that the compounds of the present invention are of value for the pre-weed emergence control of graminaceous weeds in a variety of crops, for example cotton, leguminous crops such as soyabean and peanut, and cereals such as maize. However, it will be appreciated that the individual compounds of the present invention are not all equivalent in their level of herbicidal activity and selectivity characteristics. Accordingly the optimum compound for one particular use is not necessarily the optimum compound for another particular use.

Insecticidal and miticidal tests have been carried out with a variety of compounds of the present invention. The compounds tested were found to have little or no activity against insects, for example *Plutella maculipennis, Phaedon cochlearieae,* and aphids such as Aphis fabae and *Megoura vicium.* The compounds tested were also found to have little or no activity against mites, for example *Tetranychus unticae.*

Regarding the mammalian toxicity of the compounds of the present invention, acute oral toxicity studies in mice have given satisfactory results. In these studies, the compounds of the present invention have been found to be less toxic than certain closely related 1,2,4-triazoles, for example 1-dimethylcarbamoyl-3-methylthio-1,2,4-triazole.

PREPARATION OF COMPOUNDS OF FORMULA III

The compounds of formula III may be prepared by the hereinafter described processes, which are analogous to known processes for preparing similar compounds.

One such process comprises reacting a sulphamoyltriazole of the general formula

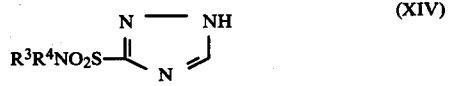

(XIV)

in whch $R^3$ and $R^4$ are as hereinbefore defined for formula III, with a carbamoyl halide of the general formula $Z-COMR^1R^2$ (XV) in which $R^1$ and $R^2$ are as hereinbefore defined for formula III and Z is chlorine, fluorine or bromine, preferably chorine. The reaction is suitably effected in the presence of an inert organic liquid as the reaction medium, which is preferably a solvent for the reactants. Advantageously the reaction is effected in the presence of a suitable acid-binding agent, for example a tertiary amine such as triethylamine or pyridine, in order to absorb the hydrogen halide produced in the reaction. In an alternative procedure, the triazole of the general formula XIV may be converted to an alkali metal (for example sodium) salt thereof prior to the reaction with the carbamoyl halide. The alkali metal salt may be obtained by reacting the triazole of the general formula XIV with an alkali metal hydride, amide or alkoxide, in accordance with known methods.

The carbamoyl halides of the general formula XV may be prepared by reacting a secondary amine of the general formula $HNR^1R^2$, in which $R^1$ and $R^2$ are as defined above, with a carbonyl halide $COZ_2$, in accordance with known methods.

The compounds of formula III may also be prepared by a process which comprises reacting a carbamoyl halide of the general formula

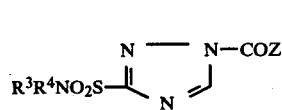

(XVI)

in which $R^3$, $R^4$ and Z are as defined above, with a secondary amine of the general formula $HNR^1R^2$, in which $R^1$ and $R^2$ are as defined above. The reaction is suitably effected in the presence of an inert organic liquid as the reaction medium, which is preferably a solvent for the reactants. Advantageously the reaction is effected in the presence of a suitable acid-binding agent, for example a tertiary amine such as triethylamine or pyridine.

The carbamoyl halides of general formula XVI may be prepared from the triazoles of general formula XIV by reaction with a carbonyl halide $COZ_2$, preferably phosgene, in accordance with known methods.

The sulphamoyltriazoles of the general formula XIV (with the exception of $NR^3R^4$=dimethylamino or 1-piperidyl), are novel compounds. The compounds may be prepared by a process which comprises reacting a 1,2,4-triazole-3-sulphonyl halide, preferably the chloride, with an amine of the general formula $HNR^3R^4$ (XVII). The reaction may be effected in an aqueous medium, or in a suitable inert organic liquid, which is preferably a solvent for the reactants. Diethyl ether and tetrahydrofuran are examples of suitable inert organic liquids that in many instances are solvents for the reactants. The reaction is preferably effected in the presence of a suitable acid-binding agent, for example triethylamine or an excess of the amine $HNR^3R^4$, in order to absorb the hydrogen halide produced in the reaction. The reaction is suitably effected at temperatures in the range 10°–30° C.

The compounds of formula III may also be prepared by a process which comprises reacting a carbonylbistriazole of the general formula

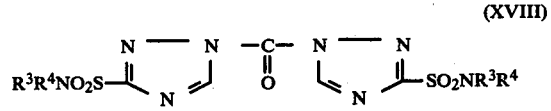

(XVIII)

in which $R^3$ and $R^4$ are as defined above, with a secondary amine of the general formula $HNR^1R^2$, in which $R^1$ and $R^2$ are as defined above. The reaction is suitably effected in the presence of an inert organic liquid as the reaction medium, which is preferably a solvent for the reactants.

The carbonylbistriazoles of the general formula XVIII may be prepared by reacting a triazole of the hereinbefore defned general formula XIV with about 0.5 molecular proportions of a carbonyl halide $COZ_2$, preferably phosgene, in accordance with known methods. The reaction is preferably effected in the presence of a suitable acid-binding agent, for example pyridine. After formation of the carbonylbistriazole, it is often convenient to react it, without isolation, with the amine of general formula $HNR^1R^2$.

It will be appreciated by those skilled in the art that the triazoles represented by the general formula XIV are tautomeric and that, for convenience, general formula XIV depicts the structure of one tautomer.

It will be appreciated by those skilled in the art that the acylation reactions described above in the preparations of compounds of formula I, II and III can theoretically give two isomeric products, one (hereinafter referred to as 1-isomer) having the general formula I, II or III and the other (hereinafter referred to as 2-isomer) having the general formula

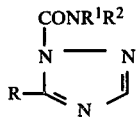

where R is the group $R^3$ of formulae I or II or the group $R^3R^4NO_2S-$ of formula III.

It is believed that the solid compounds of the present invention, after purification by standard methods such as crystallization, are obtained as substantially pure 1-isomer. The liquid compounds of the present invention, as isolated by standard methods such as distillation in vacuo, are believed to be obtained as components of an isomeric mixture consisting predominantly of the 1-isomer together with a minor proportion, generally less than about 10% of 2-isomer.

The following Examples illustrate the invention.

EXAMPLE 1

This Example illustrates the preparation of a compound of formula III.

A mixture of 6.9 g. 3-diallylsulphamoyl-1,2,4-triazole, 4.5 g. diethylcarbamoyl chloride, 6ml. triethylamine and 25 ml. dry tetrahydrofuran was refluxed under anhydrous conditions for 1.5 hours. The cooled reaction mixture was filtered to remove triethylamine hydrochloride and the filtrate was evaporated to remove solvent. The solid residue was recrystallized from petroleum ether, b.p. 60°–80° C., to give 1-diethylcarbamoyl-3-diallylsulphamoyl-1,2,4-triazole, m.p. 49°–51° C. Elemental analysis satisfactory.

The novel intermediate 3-diallylsulphamoyl-1,2,4-triazole was prepared in the following way. A stream of chlorine was passed into a solution of 20.2 g. 1,2,4-triazole-3-thiol in 330 ml. 2N hydrochloric acid, maintaining the temperature of the reaction mixture at 0° to −2° C. by means of external cooling. When excess chlorine was present (after 1.5 hours) the solid product was collected by filtration, washed with water, and sucked as dry as possible on a suction filter. There was thus obtained 1,2,4-triazole-3-sulphonyl chloride in the form of a damp solid, which was used immediately in the next stage of the preparation. This damp solid was gradually added to a stirred solution of 48.5 g. diallylamine in 100 ml. water, maintaining the temperature of the reaction mixture at 20° C. The reaction mixture was allowed to stand at 20° C. for 20 minutes, and was then acidified to pH 4.0 with concentrated hydrochloric acid. The resulting solid product was collected by filtration, washed with water, and recrystallized from water to give 3-diallylsulphamoyl-1,2,4-triazole, m.p. 131°–133° C. Elemental analysis satisfactory.

EXAMPLE 2

This Example illustrates the preparation of compounds of formula III.

By reacting the appropriate carbamoyl chloride with the appropriate 3-sulphamoyl-1,2,4-triazole in an analogous manner to that described in Example 1, the following compounds were prepared.

1-diallylcarbamoyl-3-dimethylsulphamoyl-1,2,4-triazole, m.p. 58° C.
1-(N-methyl-N-n-butylcarbamoyl)-3-dimethylsulphamoyl-1,2,4-triazole, b.p. 191°–193° C./0.5 mm.
1-diethylcarbamoyl-3-morpholinosulphonyl-1,2,4-triazole, m.p. 113°–114° C.
1-diallylcarbamoyl-3-(1-piperidylsulphonyl)-1,2,4-triazole, m.p. 72°–73° C.
1-(N-methyl-N-n-butylcarbamoyl)-3-(1-piperidylsulphonyl)-1,2,4-triazole, m.p. 70°–72° C.
1-(N-allyl-N-propylcarbamoyl)-3-(1-piperidylsulphonyl)-1,2,4-triazole, an oil, $n_D^{23}$ 1.519
1-(diethylcarbamoyl)-3-(1-piperidylsulphonyl)-1,2,4-triazole, m.p. 108°–110° C.
1-(N-methyl-N-cyclohexylcarbamoyl)-3-(1-piperidylsulphonyl)-1,2,4-triazole, m.p. 117°–118° C.
1-(N-allyl-N-ethylcarbamoyl)-3-(1-piperidylsulphonyl)-1,2,4-triazole, m.p. 50°–52° C.
1-diallylcarbamoyl-3-diallylsulphamoyl-1,2,4-triazole, an oil, $n_D^{21}$ 1.5226
1-diethylcarbamoyl-3-diallylsulphamoyl-1,2,4-triazole, m.p. 49°–51° C.
1-(N-methyl-N-cyclohexylcarbamoyl)-3-diallylsulphamoyl-1,2,4-triazole, m.p. 55°–56° C.
1-(N-allyl-N-ethylcarbamoyl)-3-diallylsulphamoyl-1,2,4-triazole, m.p. 40°–41° C.
1-(N-allyl-N-propylcarbamoyl)-3-diallylsulphamoyl-1,2,4-triazole, an oil, $n_D^{23}$ 1.513
1-diallylcarbamoyl-3-diethylsulphamoyl-1,2,4-triazole, m.p. 62°–63° C.
1-diethylcarbamoyl-3-diethylsulphamoyl-1,2,4-triazole, m.p. 105° C.
1-(N-methyl-N-cyclohexylcarbamoyl)-3-diethylsulphamoyl-1,2,4-triazole, m.p. 83°–85° C.
1-(N-allyl-N-propylcarbamoyl)-3-diethylsulphamoyl-1,2,4-triazole, m.p. 34°–35° C.
1-diallylcarbamoyl-3-pyrrolidinosulphonyl-1,2,4-triazole, m.p. 67°–68° C.
1-(N-methyl-N-cyclohexylcarbamoyl)-3-pyrrolidinosulphonyl-1,2,4-triazole, m.p. 109°–110° C.
1-diethylcarbamoyl-3-pyrrolidinosulphonyl-1,2,4-triazole, m.p. 87°–88° C.
1-(N-methyl-N-n-butylcarbamoyl)-3-pyrrolidinosulphonyl-1,2,4-triazole, m.p. 75°–76° C.
1-(N-allyl-N-propylcarbamoyl)-3-pyrrolidinosulphenyl-1,2,4-triazole, m.p. 38°–40° C.
1-(N-allyl-N-ethylcarbamoyl)-3-pyrrolidinosulphonyl-1,2,4-triazole, m.p. 61°–63° C.

By reacting 1,2,4-triazole-3-sulphonyl chloride with the appropriate amine in an analogous manner to that described in Example 1, the following novel intermediates were prepared.

3-morpholinosulphonyl-1,2,4-triazole, m.p. 227°–229° C.
3-diallylsulphamoyl-1,2,4-triazole, m.p. 131°–133° C.
3-diethylsulphamoyl-1,2,4-triazole, m.p. 143°–114° C.
3-pyrrolidinosulphonyl-1,2,4-triazole, m.p. 240°–241° C.

Satisfactory elemental analyses were obtained for all the compounds listed above.

EXAMPLE 3

This Example illustrates the preparation of compounds of formula III.

By reacting the appropriate carbamoyl chloride with the appropriate 3-sulphamoyl-1,2,4-triazole in an analogous manner to that described in Example 1, the following compounds were prepared.

1-diallylcarbamoyl-3-dipropylsulphamoyl-1,2,4-triazole, m.p. 54°–55° C.

1-diallylcarbamoyl-3-di-n-butylsulphamoyl-1,2,4-triazole, m.p. 83°-84° C.
1-diallylcarbamoyl-3-(N-ethyl-N-hexylsulphamoyl)-1,2,4-triazole, an oil, $n_D^{23}$ 1.5032
1-diallylcarbamoyl-3-(N-n-butyl-N-propylsulphamoyl)-1,2,4-triazole, an oil, $n_D^{23}$ 1.5052
1-diallylcarbamoyl-3-(2,6-dimethylmorpholinosulphonyl)-1,2,4-triazle, m.p. 87°-88.5° C.
1-diallylcarbamoyl-3-(N-methyl-N-n-butylsulphamoyl)-1,2,4-triazle, an oil, $n_D^{23}$ 1.509
1-(N-methyl-N-cyclohexylcarbamoyl)-3-(N-methyl-N-n-butylsulphamoyl)-1,2,4-triazole, m.p. 109°-110° C.
1-(N-allyl-N-ethylcarbamoyl)-3-(N-methyl-N-n-butylsulphamoyl)-1,2,4-triazole, m.p. 37°-38° C.
1-(N-allyl-N-propylcarbamoyl)-3-(N-methyl-N-n-butylsulphamoyl)-1,2,4-triazole, an oil, $n_D^{23}$ 1.501
1-diallylcarbamoyl-3-(N-methyl-N-cyclohexylsulphamoyl)-1,2,4-triazole, m.p. 68°-69.5° C.
1-diethylcarbamoyl-3-(N-methyl-N-cyclohexylsulphamoyl)-1,2,4-triazole, m.p. 74°-75° C.
1-diethylcarbamoyl-3-(N-methyl-N-sec.butylsulphamoyl)-1,2,4-triazole, m.p. 47°-50° C.
1-diallylcarbamoyl-3-(N-methyl-N-sec.butylsulphamoyl)-1,2,4-triazole, an oil, $n_D^{23}$ 15.068
1-diallylcarbamoyl-3-(N-allyl-N-methylsulphamoyl)-1,2,4-triazole, an oil, $n_D^{23}$ 1.519
1-diethylcarbamoyl-3-(N-allyl-N-methylsulphamoyl)-1,2,4-triazole, m.p. 58°-60° C.
1-(N-methyl-N-cyclohexylcarbamoyl)-3-(N-allyl-N-methylsulphamoyl)-1,2,4-triazole, m.p. 72≧-74° C.
1-(N-allyl-N-ethylcarbamoyl)-3-(N-allyl-N-methylsulphamoyl)-1,2,4-triazole, an oil, $n_D^{23}$ 1.515
1-(N-allyl-N-propylcarbamoyl)-3-(N-allyl-N-methylsulphamoyl)-1,2,4-triazole, an oil, $n_D^{23}$ 1.511
1-diallylcarbamoyl-3-[N,N-di(2-methylallyl)sulphamoyl]-1,2,4-triazole, m.p. 66°-67° C.

By reacting 1,2,4-triazole-3-sulphonyl chloride with the appropriate amine in an analogous manner to that described in Example 1, the following novel intermediates were prepared.
3-dipropylsulphamoyl-1,2,4-triazole, m.p. 111°-112° C.
3-di-n-butylsulphamoyl-1,2,4-triazole, m.p. 83°-84° C.
3-(N-ethyl-N-n-hexylsulphamoyl)-1,2,4-triazole, m.p. 100°-100.5° C.
3-(N-n-butyl-N-propylsulphamoyl)-1,2,4-triazole, m.p. 78.5°-79° C.
3-(2,6-dimethylmorpholinosulphonyl)-1,2,4-triazole, m.p. 231°-232° C.
3-(N-methyl-N-n-butylsulphamoyl)-1,2,4-triazole, m.p. 119°-120° C.
3-(N-methyl-N-cyclohexylsulphamoyl)-1,2,4-triazole, m.p. 156°-157.5° C.
3-(N-methyl-N-sec.butylsulphamoyl)-1,2,4-triazole, m.p. 132°-133° C.
3-(N-allyl-N-methylsulphamoyl)-1,2,4-triazole, m.p. 140°-142° C.
3-N,N-di(2-methylallyl)sulphamoyl-1,2,4-triazole, m.p. 151°-152° C.

Satisfactory elemental analyses were obtained for all the compounds listed above.

EXAMPLE 4

This Example illustrates the preparation of compounds of formula III.
A solution of 7.04 g. 3-dimethylsulphamoyl-1,2,4-triazole, 8 ml. triethylamine and 6.0 g. diethylcarbamoyl chloride in 25 ml. dry tetrahydrofuran was refluxed for 1½ hours.

Triethylamine hydrochloride precipitated and was filtered off. Light petroleum was added to the filtrate to precipitate the product which was separated and recrystallized from light petroleum (b.p. 80°-100° C.). The product, 1-diethylcarbamoyl-3-dimethylsulphamoyl-1,2,4-triazole had a melting point of 83° C.

The triazole intermediate used in the above reaction was prepared as follows. 50.5 g. 1,2,4-Triazole-3-thiol was suspended in 800 ml. of 2N hydrochloric acid and stirred at 0°-2° C. while a stream of chlorine was passed in. The thiol reactant passed into solution and later 1,2,4-triazole-3-sulphonyl chloride separated. After 2 hours excess of chlorine was present and the sulphonyl chloride was filtered off, washed with ice-cold water and used immediately.

The sulphonyl chloride was gradually added with stirring to 210 ml. of 25% aqueous dimethylamine at 15°-20° C. A solution resulted. After 30 minutes, acidification with hydrochloric acid precipitated the product which was recrystallized from ethanol, giving a product with a melting point 192°-194° C.

The following compounds were prepared in an analogous manner.
1-diethylcarbamoyl-3-(N-methyl-N-butylsulphamoyl)-1,2,4-triazole, m.p. 52°-53.5° C.
1-diallylcarbamoyl-3-(N-propyl-N-isopropylsulphamoyl)-1,2,4-triazole, m.p. 51°-52° C.
1-(N-methyl-N-butylcarbamoyl)-3-(N-methyl-N-butylsulphamoyl)-1,2,4-triazole, an oil, $n_D^{20}$ 1.496
1-(N-allyl-N-ethylcarbamoyl)-3-diethylsulphamoyl-1,2,4-triazole, m.p. 74°-75° C.
1-(N-ethyl-N-butylcarbamoyl)-3-(N-allyl-N-methylsulphamoyl)-1,2,4-triazole, an oil, $n_D^{20}$ 1.504
1-(N-ethyl-N-butylcarbamoyl)-3-diethylsulphamoyl-1,2,4-triazole, m.p. 56°-57.5° C.
1-(N-ethyl-N-butylcarbamoyl)-3-diallylsulphamoyl-1,2,4-triazole, an oil, $n_D^{20}$ 1.5065
1-(N-ethyl-N-butylcarbamoyl)-3-(N-methyl-N-butylsulphamoyl)-1,2,4-triazole, an oil, $n_D^{20}$ 1.495
1-(N-propyl-N-propynylcarbamoyl)-3-(N-allyl-N-methylsulphamoyl)-1,2,4-triazole, an oil, $n_D^{20}$ 1.5175 (98.6% 1-isomer by GLC assay)
1-(N-propyl-N-propynylcarbamoyl)-3-(N-methyl-N-butylsulphamoyl)-1,2,4-triazole, $n_D^{20}$ 1.5065 (97.3% 1-isomer by GLC assay)
1-(N-propyl-N-propynylcarbamoyl)-3-diallylsulphamoyl-1,2,4-triazole, m.p. 33°-34° C.
1-(N-ethyl-N-butylcarbamoyl)-3-diethylsulphamoyl-1,2,4-triazole, m.p. 56°-57.5° C.
1-(N-allyl-N-cyclohexylcarbamoyl)-3-diethylsulphamoyl-1,2,4-triazole, m.p. 71°-72° C.
1-(N-propyl-N-2-chloroethylcarbamoyl)-3-diethylsulphamoyl-1,2,4-triazole, m.p. 40°-42° C.
1-diallylcarbamoyl-3-(N-propyl-N-propynylsulphamoyl)-1,2,4-triazole, m.p. 54°-55° C.
1-diallylcarbamoyl-3-di(2-ethoxyethyl)sulphamoyl-1,2,4-triazole, an oil, $n_D^{20}$ 1.521 (97.3% 1-isomer by GLC assay)
1-diallylcarbamoyl-3-(N-propyl-N-hexylsulphamoyl)-1,2,4-triazole, an oil, $n_D^{20}$ 1.526 (96.6% 1-isomer by GLC assay)
1-(N-methyl-N-ethylcarbamoyl)-3-dimethylsulphamoyl-1,2,4-triazole, m.p. 34°-37° C.
1-(N-ethyl-N-cyclopropylcarbamoyl)-3-diethylsulphamoyl-1,2,4-triazole, m.p. 60°-62° C.

1-(N-allyl-N-hexylcarbamoyl)-3-diethylsulphamoyl-1,2,4-triazole, m.p. 42°–43° C.

1-(N-allyl-N-isopropylcarbamoyl)-3-diethylsulphamoyl-1,2,4-triazole, m.p. 64°–70° C.

1-(N-allyl-N-isopropylcarbamoyl)-3-(N-methyl-N-butylsulphamoyl-1,2,4-triazole, m.p. 35°–38° C.

1-(N-allyl-N-isopropylcarbamoyl)-3-diallylsulphamoyl-1,2,4-triazole, m.p. 32°–35° C.

1-(N-allyl-N-isopropylcarbamoyl)-3-(N-methyl-N-allylsulphamoyl-1,2,4-triazole, an oil, $n_D^{20}$ 1.515

1-di-(2-methylallyl)carbamoyl-3-diethylsulphamoyl-1,2,4-triazole, an oil, $n_D^{20}$ 1.5096 (99.8% 1-isomer by GLC assay)

1-(N-allyl-N-hexylcarbamoyl)-3-diallylsulphamoyl-1,2,4-triazole, an oil, $n_D^{20}$ 1.5075 (94.9% 1-isomer by GLC assay).

1-(N-allyl-N-hexylcarbamoyl)-3-(N-butyl-N-methylsulphamoyl)-1,2,4-triazole, an oil, $n_D^{20}$ 1.497 (95.9% 1-isomer by GLC assay).

1-diethylcarbamoyl-3-(N-hexyl-N-propylsulphamoyl)-1,2,4-triazole, m.p. 59°–60° C.

1-(N-ethyl-N-5-chloropentylcarbamoyl)-3-diethylsulphamoyl-1,2,4-triazole, an oil, $n_D^{20}$ 1.506 (88.1% 1-isomer by GLC assay).

1-diethylcarbamoyl-3-di-(2-ethoxyethyl)sulphamoyl-1,2,4-triazole, m.p. 44°–45° C.

1-(N-propyl-N-prop-2-ynylcarbamoyl)-3-diethylsulphamoyl-1,2,4-triazole, m.p. 52°–54° C.

1-di-(2-methylallylcarbamoyl)-3-diallylsulphamoyl-1,2,4-triazole, an oil, $n_D^{20}$ 1.5185

1-diethylcarbamoyl-3-dipropylsulphamoyl-1,2,4-triazole, m.p. 110° C.

1-diallylcarbamoyl-3-(N-propyl-N-2-chloroallylsulphamoyl)-1,2,4-triazole, an oil, $n_D^{23}$ 1.5200 (98.5% 1-isomer by GLC assay).

1-diallylcarbamoyl-3-[N-propyl-N-(2-methoxyethyl)sulphamoyl]-1,2,4-triazole, an oil, $n_D^{23}$ 1.5080 (99.9% 1-isomer by GLC assay)

1-diallylcarbamoyl-3-(N-allyl-N-hexylsulphamoyl)-1,2,4-triazole, an oil, $n_D^{23}$ 1.5078 (98.5% 1-isomer by GLC assay).

1-diallylcarbamoyl-3-(N-cyclopropyl-N-ethylsulphamoyl)-1,2,4-triazole, m.p. 68°–70° C.

1-diallylcarbamoyl-3-[N-allyl-N-(2-butoxyethyl)sulphamoyl]-1,2,4-triazole, an oil, $n_D^{24}$ 1.5073 (97.8% 1-isomer by GLC assay).

1-diallylcarbamoyl-3-[N-ethyl-N-(2-allyloxyethyl)sulphamoyl]-1,2,4-triazole, an oil, $n_D^{24}$ 1.5137 (99% 1-isomer by GLC assay)

1-(N-allyl-N-propylcarbamoyl)-3-(N-methyl-N-sec.-butylsulphamoyl)-1,2,4-triazole, m.p. 42°–44° C.

1-diallylcarbamoyl-3-(N-methyl-N-pentylsulphamoyl)-1,2,4-triazole, m.p. 29°–31° C.

1-diallylcarbamoyl-3-[N-propyl-N-(2-chloroallyl)sulphamoyl]-1,2,4-triazole, m.p. 42°–43° C.

1-(N-butyl-N-ethylcarbamoyl)-3-(N-methyl-N-sec.-butylsulphamoyl)-1,2,4-triazole, an oil, $n_D^{24}$ 1.4945 (94.7% 1-isomer by GLC assay)

1-diallylcarbamoyl-3-[N-ethyl-N-(2,3-dichloroallyl)sulphamoyl]-1,2,4-triazole, m.p. 25° C.

1-(N-ethyl-N-hexylcarbamoyl)-3-diethylsulphamoyl-1,2,4-triazole, m.p. 54°–55° C.

1-(N-ethyl-N-methylcarbamoyl)-3-diethylsulphamoyl-1,2,4-triazole, m.p. 49°–50° C.

1-(N-ethyl-N-methylcarbamoyl)-3-diallylsulphamoyl-1,2,4-triazole, m.p. 26°–27° C.

1-(N-ethyl-N-isopropylcarbamoyl)-3-diethylsulphamoyl-1,2,4-triazole, m.p. 80°–81° C.

1-(N-ethyl-N-isopropylcarbamoyl)-3-diallylsulphamoyl-1,2,4-triazole, m.p. 45°–46° C.

1-(N-butyl-N-methylcarbamoyl)-3-diethylsulphamoyl-1,2,4-triazole, an oil, $n_D^{20}$ 1.5005 (98.3% 1-isomer by GLC assay)

1-(N-butyl-N-methylcarbamoyl)-3-diallylsulphamoyl-1,2,4-triazole, an oil, $n_D^{20}$ 1.5115 (98.2% 1-isomer by GLC assay)

1-(N-allyl-N-isobutylcarbamoyl)-3-diethylsulphamoyl-1,2,4-triazole, m.p. 39°–40° C.

1-(N-allyl-N-butylcarbamoyl)-3-diallylsulphamoyl-1,2,4-triazole, an oil, $n_D^{20}$ 1.510 (93.0% 1-isomer by GLC assay)

1-(N-allyl-N-isobutylcarbamoyl)-3-diallylsulphamoyl-1,2,4-triazole, an oil, $n_D^{20}$ 1.509 (98.8% 1-isomer by GLC assay)

1-(N-ethyl-N-isobutylcarbamoyl)-3-diallylsulphamoyl-1,2,4-triazole, an oil, $n_D^{20}$ 1.505 (98.4% 1-isomer by GLC assay)

1-(N-ethyl-N-isobutylcarbamoyl)-3-diethylsulphamoyl-1,2,4-triazole, m.p. 55°–56° C.

1-diethylcarbamoyl-3-(N-methyl-N-pentylsulphamoyl)-1,2,4-triazole, m.p. 48°–49° C.

1-diallylcarbamoyl-3-(N-butyl-N-ethylsulphamoyl)-1,2,4-triazole, m.p. 29°–32° C.

1-diethylcarbamoyl-3-(N-butyl-N-ethylsulphamoyl)-1,2,4-triazole, m.p. 78°–79° C.

1-diallylcarbamoyl-3-(N-allyl-N-propylsulphamoyl)-1,2,4-triazole, an oil, $n_D^{22}$ 1.5168

1-(N-ethyl-N-isopentylcarbamoyl)-3-diallylsulphamoyl)-1,2,4-triazole, an oil, $n_D^{22}$ 1.5028 (96.9% 1-isomer by GLC assay)

1-(N-ethyl-N-isopentylcarbamoyl)-3-diethylsulphamoyl)-1,2,4-triazole, m.p. 78°–80° C.

1-diethylcarbamoyl-3-(N-allyl-N-propylsulphamoyl)-1,2,4-triazole, m.p. 75°–77° C.

1-(N-ethyl-N-isopentylcarbamoyl)-3-(N-butyl-N-methylsulphamoyl)-1,2,4-triazole, an oil, $n_D^{25}$ 1.4896 (95.4% 1-isomer by GLC assay)

1-(N-ethyl-N-prop-2-ynylcarbamoyl)-3-diallylsulphamoyl-1,2,4-triazole, m.p. 72°–74° C.

1-(N-ethyl-N-prop-2-ynylcarbamoyl)-3-diethylsulphamoyl-1,2,4-triazole, m.p. 104°–106° C.

1-(N-methyl-N-pentylcarbamoyl)-3-diethylsulphamoyl-1,2,4-triazole, m.p. 43°–44° C.

1-(N-methyl-N-pentylcarbamoyl)-3-diallylsulphamoyl-1,2,4-triazole, an oil, $n_D^{20}$ 1.504 (98.3% 1-isomer by GLC assay)

1-(N-ethyl-N-propylcarbamoyl)-3-diallylsulphamoyl-1,2,4-triazole, m.p. 38°–40° C.

1-(N-allyl-N-pentylcarbamoyl)-3-diethylsulphamoyl-1,2,4-triazole, m.p. 40°–41° C.

1-(N-ethyl-N-prop-2-ynylcarbamoyl)-3-(N-butyl-N-methylsulphamoyl)-1,2,4-triazole, an oil, $n_D^{26}$ 1.5073 (98.9% 1-isomer by GLC assay)

1-(N-ethyl-N-pentylcarbamoyl)-3-diallylsulphamoyl-1,2,4-triazole, an oil, $n_D^{26}$ 1.5005 (98% 1-isomer by GLC assay)

1-(N-ethyl-N-pentylcarbamoyl)-3-diethylsulphamoyl-1,2,4-triazole, an oil, $n_D^{26}$ 1.4929 (99.3% 1-isomer by GLC assay)

1-(N-ethyl-N-pentylcarbamoyl)-3-(N-butyl-N-methylsulphamoyl)-1,2,4-triazole, an oil, $n_D^{26}$ 1.4908 (99.2% 1-isomer by GLC assay)

1-(N-allyl-N-pentylcarbamoyl)-3-diallylsulphamoyl-1,2,4-triazole, an oil, $n_D^{20}$ 1.5065 (99.7% 1-isomer by GLC assay)

1-(N-ethyl-N-propylcarbamoyl)-3-(N-allyl-N-hexylsulphamoyl)-1,2,4-triazole, an oil, $n_D^{20}$ 1.495 (99.9% 1-isomer by GLC assay)

1-(N-allyl-N-ethylcarbamoyl)-3-[N-propyl-N-(2-methoxyethyl) sulphamoyl]-1,2,4-triazole, m.p. 40°–41° C.

1-(N-allyl-N-ethylcarbamoyl)-3-(N-allyl-N-propylsulphamoyl)-1,2,4-triazole, m.p. 35°–37° C.

1-(N-butyl-N-ethylcarbamoyl)-3-(N-allyl-N-propylsulphamoyl)-1,2,4-triazole, an oil, $n_D^{20}$ 1.498 (99.3% 1-isomer by GLC array)

1-(N-allyl-N-ethylcarbamoyl)-3-dimethylsulphamoyl-1,2,4-triazole, m.p. 68°–70° C.

1-(N-ethyl-N-isopropylcarbamoyl)-3-dimethylsulphamoyl)-1,2,4-triazole, m.p. 71°–74° C.

1-(N-allyl-N-isobutylcarbamoyl)-3-dimethylsulphamoyl-1,2,4-triazole, an oil, $n_D^{20}$ 1.504 (99.3% 1-isomer by GLC assay)

1-(N-allyl-N-propylcarbamoyl)-3-(N-butyl-N-ethylsulphamoyl)-1,2,4-triazole, an oil, $n_D^{20}$ 1.497 (99.7% 1-isomer by GLC assay)

1-diallylcarbamoyl-3-[N-ethyl-N-(2-methoxyethyl)sulphamoyl]-1,2,4-triazole, m.p. 32°–33° C.

1-diethylcarbamoyl-3-[N-ethyl-N-(2-methoxyethyl)sulphamoyl]-1,2,4-triazole, m.p. 74°–76° C.

1-diallylcarbamoyl-3-(N-hexyl-N-methylsulphamoyl)-1,2,4-triazole, an oil, $n_D^{23}$ 1.5070 (99.1% 1-isomer by GLC assay)

1-diethylcarbamoyl-3-(N-hexyl-N-methylsulphamoyl)-1,2,4-triazole, m.p. 63°–64° C.

1-(N-allyl-N-methylcarbamoyl)-3-diallylsulphamoyl-1,2,4-triazole, an oil, $n_D^{27}$ 1.5192 (98.8% 1-isomer by GLC assay)

1-(N-allyl-N-methylcarbamoyl)-3-diethylsulphamoyl-1,2,4-triazole, m.p. 59°–61° C.

1-(N-allyl-N-methylcarbamoyl)-3-(N-butyl-N-methylsulphamoyl)-1,2,4-triazole, an oil, $n_D^{27}$ 1.5055 (99.9% 1-isomer by GLC assay)

1-diethylcarbamoyl-3-dibutylsulphamoyl-1,2,4-triazole, m.p. 90°–91° C.

1-diallylcarbamoyl-3-(N-ethyl-N-pentylsulphamoyl)-1,2,4-triazole, m.p. 38°–39° C.

1-diethylcarbamoyl-3-(N-ethyl-N-pentylsulphamoyl)-1,2,4-triazole, m.p. 86°–87° C.

1-diethylcarbamoyl-3-di-(2-methylallyl)sulphamoyl-1,2,4-triazole, m.p. 84°–85° C.

1-diallylcarbamoyl-3-(N-allyl-N-ethylsulphamoyl)-1,2,4-triazole, an oil, $n_D^{22}$ 1.5192 (99.9% 1-isomer by GLC assay)

1-(N-ethyl-N-sec.butylcarbamoyl)-3-diallylsulphamoyl-1,2,4-triazole, an oil, $n_D^{26}$ 1.5045 (96.4% 1-isomer by GLC assay)

1-(N-ethyl-N-sec.butylcarbamoyl)-3-diethylsulphamoyl-1,2,4-triazole, an oil, $n_D^{26}$ 1.4952 (94.6% 1-isomer by GLC assay)

1-(N-ethyl-N-sec.butylcarbamoyl)-3-(N-butyl-N-methylsulphamoyl)-1,2,4-triazole, an oil, $n_D^{26}$ 1.4928 (94.8% 1-isomer by GLC assay)

1-(N-methyl-N-hexylcarbamoyl)-3-(N-butyl-N-methylsulphamoyl)-1,2,4-triazole, an oil, $n_D^{27}$ 1.4912 (99.3% 1-isomer by GLC assay)

1-(N-ethyl-N-isopropylcarbamoyl)-3-(N-butyl-N-ethylsulphamoyl)-1,2,4-triazole, m.p. 39°–41° C.

1-diethylcarbamoyl-3-(N-ethyl-N-methylsulphamoyl)-1,2,4-triazole, m.p. 61°–62° C.

1-diallylcarbamoyl-3-(N-ethyl-N-methylsulphamoyl)-1,2,4-triazole, an oil, $n_D^{20}$ 1.515 (99.9% 1-isomer by GLC assay)

1-(N-allyl-N-propylcarbamoyl)-3-(N-ethyl-N-methylsulphamoyl)-1,2,4-triazole, an oil, $n_D^{20}$ 1.504 (99.2% 1-isomer by GLC assay)

1-(N-butyl-N-ethylcarbamoyl)-3-(N-ethyl-N-methylsulphamoyl)-1,2,4-triazole, an oil, $n_D^{20}$ 1.495 (99.3% 1-isomer by GLC assay)

1-diethylcarbamoyl-3-(N-allyl-N-ethylsulphamoyl)-1,2,4-triazole, m.p. 58°–60° C.

1-diethylcarbamoyl-3-(N-ethyl-N-propylsulphamoyl)-1,2,4-triazole, m.p. 97°–100° C.

1-diallylcarbamoyl-3-(N-ethyl-N-propylsulphamoyl)-1,2,4-triazole, m.p. 44°–45° C.

1-(N-butyl-N-ethylcarbamoyl)-3-(N-ethyl-N-propylsulphamoyl)-1,2,4-triazole, m.p. 58°–59° C.

1-(N-methyl-N-propylcarbamoyl)-3-diethylsulphamoyl-1,2,4-triazole, m.p. 54°–55° C.

1-(N-methyl-N-propylcarbamoyl)-3-(N-butyl-N-methylsulphamoyl)-1,2,4-triazole, an oil, $n_D^{23}$ 1.5025 (99.0% 1-isomer by GLC assay)

1-(N-methyl-N-propylcarbamoyl)-3-diallylsulphamoyl-1,2,4-triazole, an oil, $n_D^{23}$ 1.5160 (98.5% 1-isomer by GLC assay)

1-diethylcarbamoyl-3-(N-methyl-N-isobutylsulphamoyl)-1,2,4-triazole, m.p. 84°–86° C.

1diallylcarbamoyl-3-(N-pentyl-N-propylsulphamoyl)-1,2,4-triazole, m.p. 43°–44° C.

1-diethylcarbamoyl-3-(N-pentyl-N-propylsulphamoyl)-1,2,4-triazole, m.p. 72°–73° C.

1-diethylcarbamoyl-3-(N-propyl-N-isopropylsulphamoyl)-1,2,4-triazole, m.p. 106°–108° C.

1-diallylcarbamoyl-3-(N-isobutyl-N-methylsulphamoyl)-1,2,4-triazole, m.p. 63°–64° C.

1-(N-allyl-N-ethylcarbamoyl)-3-[N-methyl-N-(4-fluorophenyl) sulphamoyl]-1,2,4-triazole, m.p. 68°–71° C.

1-(N-ethyl-N-pentylcarbamoyl)-3-[N-methyl-N-(4-fluorophenyl) sulphamoyl]-1,2,4-triazole, an oil, $n_D^{27}$ 1.5223

1-(N-allyl-N-methylcarbamoyl)-3-[N-methyl-N-(4-fluorophenyl) sulphamoyl]-1,2,4-triazole, an oil, $n_D^{27}$ 1.5425

1-(N-ethyl-N-sec.butylcarbamoyl)-3-[N-methyl-N-(4-fluorophenyl)sulphamoyl]-1,2,4-triazole, an oil, $n_D^{26}$ 1.5260

1-(N-hexyl-N-methylcarbamoyl)-3-[N-methyl-N-(4-fluorophenyl) sulphamoyl]-1,2,4-triazole, an oil, $n_D^{26}$ 1.5222

1-(N-ethyl-N-propylcarbamoyl)-3-[N-methyl-N-(4-fluorophenyl) sulphamoyl]-1,2,4-triazole, m.p. 80°–82° C.

1-(N-butyl-N-ethylcarbamoyl)-3-[N-methyl-N-(4-fluorophenyl) sulphamoyl]-1,2,4-triazole, m.p. 48°–52° C.

1-(N-allyl-N-propylcarbamoyl)-3-[N-methyl-N-(4-fluorophenyl) sulphamoyl]-1,2,4-triazole, m.p. 76°–77° C.

1-(N-butyl-N-methylcarbamoyl)-3-[N-methyl-N-(4-fluorophenyl) sulphamoyl]-1,2,4-triazole, m.p. 87°–89° C.

1-(N-methyl-N-cyclohexylcarbamoyl)-3-[N-methyl-N(4-fluorophenyl)sulphamoyl]-1,2,4-triazole, m.p. 117°–118° C.

1-(N-allyl-N-isobutylcarbamoyl)-3-[N-methyl-N-(4-fluorophenyl)sulphamoyl]-1,2,4-triazole, an oil, $n_D^{20}$ 1.530 (99.7% isomer by GLS assay)

1-(N-methyl-N-propylcarbamoyl)-3-[N-methyl-N-(4-fluorophenyl) sulphamoyl]-1,2,4-triazole, m.p. 71°–72.5° C.

1-diallycarbamoyl-3-[N-methyl-N-(4-fluorophenyl)sulphamoyl]-1,2,4-triazole, m.p. 75°–76° C.
1-diethylcarbamoyl-3-[N-ethyl-N-(4-fluorophenyl)sulphamoyl]-1,2,4-triazole, m.p. 121°–123° C.
1-diallylcarbamoyl-3-[N-ethyl-N-(4-chlorophenyl)sulphamoyl]-1,2,4-triazole, m.p. 61°–63° C.
1-diethylcarbamoyl-3-[N-ethyl-N-(4-chlorophenyl)sulphamoyl]-1,2,4-triazole, m.p. 99°–101° C.

Satisfactory elemental analyses were obtained for all the compounds listed above.

The following novel intermediate triazoles were prepared.

3-(N-propyl-N-isopropylsulpamoyl)-1,2,4-triazole, m.p. 167°–168° C.
3-di-(2-ethoxyethyl)sulphamoyl-1,2,4-triazole, m.p. 79°–80° C.
3-(N-propyl-N-hexylsulphamoyl)-1,2,4-triazole, m.p. 70°–72° C.
3-(N-propyl-N-prop-2-ynylsulphamoyl)-1,2,4-triazole, m.p. 164°–166° C.
3-(N-propyl-N-2-chloroallylsulphamoyl)-1,2,4-triazole m.p. 137°–138° C.
3-[N-propyl-N-(2-methoxyethyl)sulphamoyl]-1,2,4-triazole m.p. 86°–88° C.
3-(N-allyl-N-hexylsulphamoyl)-1,2,4-triazole m.p. 95°–96° C.
3-(N-cyclopropyl-N-ethylsulphamoyl)-1,2,4-trizole m.p. 153°–155° C.
3-[N-allyl-N-(2-butoxyethyl)sulphamoyl]-1,2,4-triazole m.p. 69°–71° C.
3-[N-ethyl-N-(2-allyloxyethyl)sulphamoyl]-1,2,4-traizole m.p. 124°–125° C.
3-(N-methyl-N-pentylsulphamoyl)-1,2,4-triazole m.p. 124°–125° C.
3-[N-ethyl-N-(2,3-dichloroallyl)sulphamoyl]-1,2,4-triazole m.p. 116°–117° C.
3-(N-butyl-N-ethylsulphamoyl)-1,2,4-triazole, m.p. 101°–103° C.
3-(N-allyl-N-propylsulphamoyl)-1,2,4-triazole, m.p. 125°–127° C.
3-[N-ethyl-N-(2-methoxyethyl)sulphamoyl]-1,2,4-triazole m.p. 102°–104° C.
3-(N-methyl-N-hexylsulphamoyl)-1,2,4-triazole, m.p. 123°–124° C.
3-(N-ethyl-N-pentylsulphamoyl)-1,2,4-triazole, m.p. 111°–113° C.
3-(N-ethyl-N-methylsulphamoyl)-1,2,4-triazole, m.p. 277°–124° C.
3-(N-allyl-N-ethylsulphamoyl)-1,2,4-triazole, m.p. 131°–132° C.
3-(N-ethyl-N-propylsulphamoyl)-1,2,4-triazole, m.p. 120°–123° C.
3-(N-methyl-N-isobutylsulphamoyl)-1,2,4-triazole, m.p. 150°–151° C.
3-(N-propyl-N-pentylsulphamoyl)-1,2,4-triazole, m.p. 61°–62° C.
3-[N-methyl-N-(4-fluorophenyl)sulphamoyl]-1,2,4-triazole, m.p. 137.5°–138.5° C.
3-[N-methyl-N-(4-chlorophenyl)sulphamoyl]-1,2,4-triazole, m.p. 156°–157° C.

EXAMPLE 5

Thin Example illustrates the preparation of compounds of formula III.

A solution of 8.64 g. piperidinosulphonyl-1,2,4-trazole, 8 ml. triethylamine and 6.0 g. diethylcarbamoyl chloride in 25 ml. dry tetrahydrofuran was refluxed for 1½ hours.

Triethylamine hydrochloride precipitated and was filtered off. Light petroleum was added to the filtrate to precipitate the product which was separated and recrystallized from light petroleum (b.p. 80°–100° C.). The product 1-diethylcarbamoyl-3-piperidinosulphonyl-1,2,4-triazole had a melting point of 108°–110° C.

The triazole intermediate used in the above reaction was prepared as follows. Firstly the 1,2,4-triazole-3-sulphonyl chloride was prepared as in Example 4. The sulphonyl chloride thus prepred was gradually added with stirring to 100 ml. of water and 85 g. piperidine maintained at 15°–20° C. A solution resulted. After 30 minutes, acidification with hydrochloric acid precipitated the product which was recrystallized from ethanol, giving a product with a melting point 196°–198° C.

The following compounds were prepared in an analogous manner.

1-diethylcarbamoyl-3-(2,6-imethylmorpholinosulphonyl)-1,2,4-triazole, m.p. 116°–120° C.
1-(N-ethyl-N-butylcarbamoyl)-3-piperidinosulphonyl-1,2,4-triazole, an oil, $n_D^{20}$ 1.512
1-(N-propyl-N-propynylcarbamoyl)-3-piperidinosulphonyl-1,2,4-triazole, an oil, $n_D^{20}$ 1.5275
1-diallylcarboamoyl-3-hexamethyleneiminosulphonyl-1,2,4-triazole, m.p. 40°–41° C.
1-diallylcarbamoyl-3-(4-methylpiperidino)sulphonyl-1,2,4-triazol, m.p. 64°–65° C.
1-diallylcarbamoyl-3-heptamethyleneiminosulphenyl-1,2,4-triazole, m.p. 54°–55° C.
1-(N-methyl-N-ethylcarbamoyl)-3-pyrrolidinosulphonyl-1,2,4-triazole, m.p. 83°–84° C.
1-(N-ethyl-N-isopentylcarbamoyl)-3-piperidinosulphonyl-1,2,4-triazole, an oil, $n_D^{25}$ 1.4896 (96.3% 1-isomer by GLC assay)
1-(N-ethyl-N-prop-2-ynylcarbamoyl)-3-piperidinosulphoneyl-1,2,4-triazole, m.p. 92°–94° C.
1-(N-ethyl-N-pentylcarbamoyl)-3-piperidinosulphonyl-1,2,4-triazole, an oil, $n_D^{26}$ 1.5078 (98.8% 1-isomer by CLC assay)
1-(N-allyl-N-methylcarbamoyl)-3-piperidinosulphonyl-1,2,4-triazole, an oil, $n_D^{27}$ 1.5266 (99.6% 1-isomer by GLC assay)
1-(N-ethyl-N-secbutylcarbamoyl)-3-piperidinosulphonyl-1,2,4-triazole, an oil, $n_D^{25}$ 1.5086 (95.3% 1-isomer by GLC assay)
1-(N-hexyl-N-methylcarbamoyl)-3-(piperidinosulphonyl-1,2,4-triazole, an oil, $n_D^{26}$ 1.5070 (97.8% 1-isomer by GLC assay)
1-(N-methyl-N-propylcarbamoyl)-3-piperidinosulphonyl-1,2,4-triazole, m.p. 91°–92.5° C. Satisfactory elemental analyses were obtained for all the compounds listed above.

The following novel intermediate triazoles were prepared:

3-hexamethyleneiminosulphonyl-1,2,4-triazole, m.p. 203°–204° C.
3-(4-methylpiperidyl)sulphonyl-1,2,4-triazole, m.p. 230°–232° C.
3-heptamethyleneiminosulphonyl-1,2,4-triazole, m.p. 225°–227° C.
3-pyrrolidinosulphonyl-1,2,4-triazole
3-(2,6-dimethylmorpholinosulphonyl-1,2,4-triazole

EXAMPLE 6

This Example illustrates the preparation of compounds of formula III.

A solution of 6.9 g. 3-diallylsulphamoyl-1,2,4-triazole, 6 ml. triethylamine and 5.9 g. N-propyl-N-(2-chloroallyl)carbamoyl chloride in 25 ml. dry tetrahydrofuran was refluxed for two hours.

Triethylamine hydrochloride precipitated and was filtered off. The filtrate was diluted with ether, washed twice with ice-cold 0.1N sodium hydroxide solution and once with water, dried over sodium sulphate and distilled to dryness, finally at 100° C./0.5 mm. The product 1-[N-propyl-N-(2-chloroallyl)carbamoyl]-3-diallylsulphamoyl-1,2,4-triazole was a viscous oily residue, $n_D^{20}$ 1.5230.

The following compounds were prepared in an analogous manner;

1-[N-propyl-N-(2-chloroallyl)carbamoyl]-3-diethylsulphamoyl-1,2,4-triazole, m.p. 50° C.

1-[N-propyl-N(2-chloroallyl)carbamoyl]-3-(N-methyl-N-allylsulphamoyl)-1,2,4-triazole, an oil, $n_D^{20}$ 1.5216 (98.9% 1-isomer by GLC assay)

1-[N-ethyl-N-(2,3dichloroallyl)carbamoyl]-3-diethylsulphamoyl-1,2,4-triazole, an oil $n_D^{20}$ 1.5282 (98.6% 1-isomer by GLC assay)

1-[N-propyl-N(2-chloroallyl)carbamoyl]-3-(N-methyl-N-butylsulphamoyl)-1,2,4-triazole, an oil, $n_D^{20}$ 1.512

1-[N-ethyl-N-(2-chloroallyl)carbamoyl]-3-diallylsulphamoyl-1,2,4-triazole, m.p. 63°–64° C.

1-[N-ethyl-N-(2-chloroallyl)carbamoyl]-3-diethylsulphamoyl-1,2,4-triazole, m.p. 57°–88° C.

1-[N-allyl-N-(2-chloroallyl)carbamoyl]-3-diethylsulphamoyl-1,2,4-triazole, m.p. 57°–58° C.

1-[N-allyl-N-(2-chloroallyl)carbamoyl]-3-dimethylsulphamoyl-1,2,4-triazole, an oil, $n_D^{20}$ 1.527 (97.9% 1-isomer by GLC assay)

1-[N-ethyl-N-(2-chloroallyl)carbamoyl]-3-N-methyl-N-(4-fluorophenyl)sulphamoyl-1,2,4-triazole, an oil, $n_D^{20}$ 1.547 (94.9% 1-isomer by GLC assay)

Satisfactory elemental analyses were obtained for all the compounds listed above.

EXAMPLE 7

This Example illustrates the preparation of compounds of formula III.

A solution of 0.03 mole 3-diallylsulphamoyl-1,2,4-triazole, 8 ml. triethylamine and 0.03 mole of N-ethyl-N-2-methoxyethylcarbamoyl chloride in 40 ml. of dry tetrahydrofuran was held at room temperature for 3 days. The amine hydrochloride was filtered off and the solvent removed by evaporation. 100 ml. of petroleum ether were added to the mixture and petroleum ether decanted from the liquid layer formed. This was then dissolved in ether, filtered and the solvent removed by evaporation on the steam bath. The liquid product, 1-[N-ethyl-N-(2-methoxyethyl)carbamoyl]-3-diallylsulphamoyl-1,2,4-triazole was heated at 100° C. in vacuo for 3 hours at a pressurre of lower than 0.2 mm. in order to remove all traces of carbamoyl chloride. The compound which was an oily liquid had a refractive index $n_D^{23}$ 1.5100. Assay by GLC showed that 96.1% of 1-isomer was present. Elemental analysis was satisfactory.

The 3-diallylsulphamoyl-1,2,4-triazole intermediate used in the above preparation was prepared as in Example 4.

The preparation of the carbamoyl chloride reactant was as follows.

N-ethyl-N-2-methoxyethylamine, b.p. 115°–116° C. was first prepared by reaction of 3 molecular proportions of ethylamine with 1 molecular proportion of 1-bromo-2-methoxyethane in aqueous solution containing 1 equivalent of sodium hydroxide at 30°–50° C.

To a stirred solution of 89.1 g. phosgene in 500 ml. dry ether at $-20°$ C. was added a solution of 30.9 g. N-ethyl-N-2-methoxyethylamine in 50 ml. dry ether, whilst the temperature of the reaction mixture was maintained at $-20°$ C. The stirred mixture was then allowed to warm to room temperature during 1 hour. The reaction mixture was filtered and the filtrate evaporated in vacuo below 25° C. to remove the solvent and give the product, N-2-methoxyethyl)-N-ethylcarbamoyl chloride as a pale yellow liquid.

The following compounds were prepared in an analogous manner.

1-[N-ethyl-N-(2-allyloxyethyl)carbamoyl]-3-diethylsulphamoyl-1,2,4-triazole, an oil, $n_D^{22}$ 1.5035 (98.4% 1-isomer by GLC assay)

1-[N-propyl-N-(2-methoxyethyl)carbamoyl]-3-diethylsulphamoyl-1,2,4-triazole, an oil, $n_D^{22}$ 1.4982 (97.5% 1-isomer by GLC assay)

1-[N-ethyl-N-(2-methoxyethyl)carbamoyl]-3-diallylsulphamoyl-1,2,4-triazole, an oil, $n_D^{23}$ 1.5100 (96.7% 1-isomer by GLC assay)

1-[N-ethyl-N-(2-methoxyethyl)carbamoyl]-3-diethylsulphamoyl-1,2,4-triazole, an oil, $n_D^{23}$ 1.5005 (96.8% 1-isomer by GLC assay)

1-[N-ethyl-N-(3-methoxypropyl)carbamoyl]-3-diethylsulphamoyl-1,2,4-triazole, an oil, $n_D^{22}$ 1.4965 (97.0% 1-isomer by GLC assay)

1-[N-ethyl)-N-(3-methoxypropyl)carbamoyl]-3-diallylsulphamoyl-1,2,4-triazole, an oil, $n_D^{22}$ 1.5061 (96.6% 1-isomer by GLC assay)

1-(N-propyl-N-methoxymethylcarbamoyl)-3-diethylsulphamoyl-1,2,4-triazole, m.p. 37.5°–38.5° C.

1-[N-propyl-N-(2-methoxyethyl)carbamoyl]-3-diallylsulphamoyl-1,2,4-triazole, an oil, $n_D^{28}$ 1.5025 (95.9% 1-isomer by GLC assay)

1-[N-propyl-N-(2-methoxyethyl)carbamoyl]-3-(N-butyl-N-methylsulphamoyl)-1,2,4-triazole, an oil, $n_D^{28}$ 1.4914 (96.0% 1-isomer by GLC assay)

1-[N-propyl-N-(2-methoxyethyl)carbamoyl]-3-piperidinosulphonyl-1,2,4-triazole, m.p. 73.5°–75.5° C.

1-[N-propyl-N-(2-methoxyethyl)carbamoyl]-3-[N-methyl-N-(4-fluorophenyl)sulphamoyl]-1,2,4-triazole, an oil, $n_D^{28}$ 1.5224

1-[N-propyl-N-(2-ethoxtyethyl)carbamoyl]-3-diethylsulphamoyl-1,2,4-triazole, an oil, $n_D^{23}$ 1.4925 (97.1% 1-isomer by GLC assay)

1-[N-propyl-N-(2-ethoxyethyl)carbamoyl]-3-(N-butyl-N-methylsulphamoyl-1,2,4-triazole, an oil, $n_D^{23}$ 1.4900 (97.1% 1-isomer by GLC assay)

1-[N-ethyl-N-(2-ethoxyethyl)carbamoyl]-3-diallylsulphamoyl-1,2,4-triazole, an oil, $n_D^{23}$ 1.5026 (98.1% 1-isomer by GLC assay)

1-[N-ethyl-N-(2-ethoxyethyl)carbamoyl]-3-diethylsulphamoyl-1,2,4-triazole, an oil, $n_D^{23}$ 1.4930 (98.1% 1-isomer by GLC assay)

1-[N-ethyl-N-(2-ethoxyethyl)carbamoyl]-3-(N-butyl-N-methylsulphamoyl)-1,2,4-triazole, an oil, $n_D^{23}$ 1.4910 (97.8% 1-isomer by GLC assay)

1-[N-ethyl-N-(2-ethoxyethylcarbamoyl]-3-piperidinosulphonyl-1,2,4-triazole, m.p. 73.5°–77.5° C.

Satisfactory elemental analyses were obtained for all of the compounds listed above.

EXAMPLE 74

This Example illustrates compositions comprising a compound of formula III.

A dispersible powder was prepared by grinding together a mixture of the following ingredients in a hammer mill.

| | % w/w |
|---|---|
| 1-Diallylcarbamoyl-3-(1-piperidylsulphonyl)-1,2,4-triazole | 25.0 |
| Sodium N-methyl-N-palmitoyltaurate | 6.0 |
| Sodium di-octylsulphosuccinate | 0.5 |
| Colloidal silicic acid | 25.0 |
| Kaolin | 43.5 |

Similar dispersible powders were prepared using the following active ingredients in place of the triazole compound in the above formulation.

1-diallylcarbamoyl-3-dipropylsulphamoyl-1,2,4-triazole
1-diallylcarbamoyl-3-pyrrolidinosulphonyl-1,2,4-triazole
1-diethylcarbamoyl-3-diallylsulphamoyl-1,2,4-triazole
1-diallylcarbamoyl-3-diethylsulphamoyl-1,2,4-triazole
1-(N-allyl-N-ethylcarbamoyl)-3-(1-piperidylsulphonyl)-1,2,4-triazole
1-(N-methyl-N-cyclohexylcarbamoyl)-3-diethylsulphamoyl-1,2,4-triazole
1-(N-methyl-N-cyclohexylcarbamoyl)-3-diallylsulphamoyl-1,2,4-triazole
1-diallylcarbamoyl-3-(1-piperidylsulphonyl)-1,2,4-triazole

EXAMPLE 9

This Example illustrates compositions comprising a compound of formula III.

An emulsifiable concentrate suitable for dilution with water to form an aqueous emulsion was prepared from the following ingredients.

| | % w/v |
|---|---|
| 1-Diallylcarbameyl-3-(N-allyl-N methylsulphamoyl)-1,2,4-triazole | 20.0 |
| Calcium dodecylbenzenesulphonate | 2.5 |
| Nonylphenoxypolyethoxyethanol* | 2.5 |
| Xylene | to 100.0 |

*A nonylphenol-ethylene oxide condensate containing an average of 14 mols. ethylene oxide per mol. nonylphenol.

A similar emulsifiable concentrate was prepared in which the triazole compound in the above formulation was replaced by the following compound.
1-(N-allyl-N-propylcarbamoyl)-3-diethylsulphamoyl-1,2,4-triazole.

EXAMPLE 10

This Example illustrates the use of compositions comprising a compound of formula III.

In tests carried out in the glasshouse, trays of soil were sown with seeds of various weeds and then immediately sprayed with aqueous suspension of compounds under test at various application rates of test compound. Seeded trays of soil receiving no chemical treatment were used as control. At an application rate of 0.5 lb./acre, all the triazoles mentioned in Example 8 and 9 controlled the weeds crabgrass, barnyard grass, yellow foxtail and Johnson grass (no germination or emergent seedlings severely and irrecoverable stunted).

EXAMPLE 11

This Example illustrates the use of herbicidal compositions comprising a compound of the formula III.

Compositions were prepared containing the following compounds as active ingredients:
1-(N-butyl-N-ethylcarbamoyl)-3-(N-allyl-N-methylsulphamoyl)-1,2,4-triazole.
1-(N-ethyl-N-methylcarbamoyl)-3-pyrrolidinosulphonyl-1,2,4-triazole.
1-(N-allyl-N-ethylcarbamoyl)-3-diallylsulphamoyl-1,2,4-triazole.
1-diethylcarbamoyl-3-diallylsulphamoyl-1,2,4-triazole.
1-(N-allyl-N-propylcarbamoyl)-3-diethylsulphamoyl-1,2,4-triazole.

Rice seedlings were grown under paddy conditions in the glasshouse. At the 2-3 leaf stage the trays containing the seedlings were seeded with barnyard grass and then sprayed with aqueous emulsions prepared from the above concentrates, at an application rate of active ingredient of ¼ lb./acre. After seven days the trays were flooded with water and examined 21 days after spraying.

No barnyard grass was observed in the trays sprayed with the gaseous emulsions described above, and no lasting phytotoxic effect on the rice plants was observed. A growth of barnyard grass had occurred in control trays that had received no chemical treatment.

We claim:

1. A compound of the general formula $$\begin{array}{c} N \longrightarrow N-CONR^1R^2 \\ R^3R^4NO_2S-\!\!\!\!\!\!\!\parallel \quad \parallel \\ N \end{array}$$

in which $R^1$ is alkyl containing 1-2 carbon atoms, allyl, 2-methylallyl, prop-2-ynyl, alkoxyalkyl containing 2-4 carbon atoms, haloalkyl containing 1-4 carbon atoms, 2-haloallyl, 2,3-dihaloallyl or cyclopropyl, $R^2$ is alkyl containing 2-8 carbon atoms, alkenyl containing 2-8 carbon atoms, alkenyloxyalkyl containing 4-8 carbon atoms, haloalkyl containing 2-8 carbon atoms, 2-haloallyl, 2,3-dihaloallyl, cyclopropyl or cyclohexyl, $R^3$ is alkyl containing 1-4 carbon atoms, allyl, 2-methylallyl, prop-2-ynyl, alkoxyalkyl containing 2-4 carbon atoms, haloalkyl containing 1-4 carbon atoms, 2-haloallyl, 2,3-dihaloallyl, cyclopropyl or phenyl containing 1-3 halo substituents, $R^4$ is alkyl containing 1-8 carbon atoms, alkenyl containing 2-8 carbon atoms, alkoxyalkyl containing 2-8 carbon atoms, alkenyloxyalkyl containing 4-8 carbon atoms, haloalkyl containing 1-8 carbon atoms, 2-haloallyl, 2,3-dihaloallyl, cyclopropyl or cyclohexyl, or $R^3$ and $R^4$, together with the nitrogen atom to which they are attached, form a heterocyclic ring, optionally containing 1-4 lower alkyl substituents, selected from morpholino, pyrrolidino, 1-piperidinyl, hexamethyleneimino and heptamethyleneimino, provided that the total number of carbon atoms is $R^1$ and $R^2$ together is 3-9 inclusive, and when $R^3$ is a radical not containing a phenyl nucleus, the total number of carbon atoms in $R^3$ and $R^4$ together is 2-9 inclusive.

2. A compound according to claim 1 in which $R^1$ is alkyl containing 1-2 carbon atoms, allyl, 2-methylallyl, prop-2-ynyl, alkoxyalkyl containing 2-4 carbon atoms, haloalkyl containing 2-4 carbon atoms, 2-haloallyl, 2,3-dihaloallyl or cyclopropyl, $R^2$ is alkyl containing 2-8 carbon atoms, allyl, 2-methylallyl, allyloxyalkyl containing 5-8 carbon atoms, haloalkyl containing 2-4 carbon atoms, 2-haloallyl, cyclopropyl or cyclohexyl, $R^3$ is alkyl containing 1-4 carbon atoms, allyl, 2-methylallyl, prop-2-ynyl, alkoxyalkyl containing 3-4 carbon atoms, haloalkyl containing 2-4 carbon atoms, 2-haloallyl, 2,3-dihaloallyl, cyclopropyl or phenyl containing a single halo substituent, and $R^4$ is alkyl containing 1-8 carbon atoms, allyl, 2-methylallyl, alkoxyalkyl containing 3-8 carbon atoms, allyloxyalkyl containing 5-8 carbon atoms, haloalkyl containing 2-8 carbon atoms, 2-haloallyl, 2,3-dihaloallyl, cyclopropyl or cyclohexyl, or $R^3$ and $R^4$, together with the nitrogen atom to which they are attached, form a heterocyclic ring, optionally containing the 1-4 methyl substituents, selected from morpholino, pyrrolidino, 1-piperidyl, hexamethyleneimino and heptamethyleneimino.

3. A compound according to claim 2 in which $R^1$ is alkyl containing 1-2 carbon atoms, allyl, 2-methylallyl, prop-2-ynyl or alkoxyalkyl containing 2-4 carbon atoms and $R^2$ is alkyl containing 2-8 carbon atoms, allyl or 2-methylallyl.

4. A compound according to claim 3 in which $R^3$ is alkyl containing 1-4 carbon atoms, allyl, 2-methylallyl, alkoxyalkyl containing 3-4 carbon atoms, phenyl containing a single halosubstituent and $R^4$ is alkyl containing 1-8 carbon atoms, allyl, 2-methylallyl or alkoxyalkyl containing 3-8 carbon atoms.

5. A compound according to claim 1 in which the carbamoyl group $CONR^1R^2$ is diallylcarbamoyl and the sulphamoyl group $SO_2NR^3R^4$ is dialkylsulphamoyl, di-(2-methylallyl)sulphamoyl or N-allyl-N-alkylsulphamoyl.

6. A compound according to claim 1 in which the carbamoyl group $CONR^1R^2$ is dialkylcarbamoyl and the sulphamoyl group $SO_2NR^3R^4$ is dialkylsulphamoyl, diallylsulphamoyl or N-allyl-N-alkylsulphamoyl.

7. A compound according to claim 1 in which the cabamoyl group $CONR^1R^2$ is N-allyl-N-alkylcarbamoyl and the sulphamoyl group $SO_2NR^3R^4$ is dialkylsulphamoyl, diallylsulphamoyl or N-allyl-N-alkylsulphamoyl.

8. A compound according to claim 1 in which the carbamoyl group $CONR^1R^2$ is N-alkyl-N-alkoxyalkylcarbamoyl and the sulphamoyl group $SO_2NR^3R^4$ is dialkylsulphamoyl, diallylsulphamoyl or N-allyl-N-alkylsulphamoyl.

9. A herbicidal composition which comprises as an active ingredient a herbicidally effective amount of a triazole of the general formula defined in claim 1 in association with a diluent or carrier.

10. A herbicidal composition according to claim 9 in which the diluent or carrier is a solid or a liquid containing a surface-active agent.

11. A method for the pre-weed emergence control of graminaceous weeds which comprises applying to the locus of the weeds a herbicidally effective amount of a triazole of the general formula defined in claim 1.

12. A method according to claim 11 for selectively controlling graminaceous weeds in a crop area in which the triazole is applied to a crop area at an application rate sufficient to control the weeds but substantially non-phytotoxic to the crop.

13. A method according to claim 12 in which the weeds crabgrass, barnyard grass, yellow foxtail and Johnson grass are controlled in a crop area selected from cotton, soyabean, maize and peanut.

14. A method according to claim 13 in which the crops are selected from cotton, soyabean and peanut.